US007928294B2

(12) United States Patent
Fukuzawa et al.

(10) Patent No.: US 7,928,294 B2
(45) Date of Patent: Apr. 19, 2011

(54) POLYPEPTIDE HAVING Δ5 DESATURATING ACTIVITY, POLYNUCLEOTIDE CODING FOR THE POLYPEPTIDE, AND USE THEREOF

(75) Inventors: Hideya Fukuzawa, Kyoto (JP); Katsuyuki Yamato, Kyoto (JP); Masataka Kajikawa, Mie (JP)

(73) Assignee: Suntory Holdings Limited, Osaka-shi, Osaka (JP)

( * ) Notice: Subject to any disclaimer, the term of this patent is extended or adjusted under 35 U.S.C. 154(b) by 901 days.

(21) Appl. No.: 11/632,116

(22) PCT Filed: Jul. 11, 2005

(86) PCT No.: PCT/JP2005/013200
§ 371 (c)(1),
(2), (4) Date: Aug. 1, 2007

(87) PCT Pub. No.: WO2006/006710
PCT Pub. Date: Jan. 19, 2006

(65) Prior Publication Data
US 2008/0060100 A1    Mar. 6, 2008

(30) Foreign Application Priority Data

Jul. 12, 2004 (JP) ................................. 2004-205325
Feb. 21, 2005 (JP) ................................. 2005-044129

(51) Int. Cl.
*A01H 5/00* (2006.01)
*C12N 15/82* (2006.01)
*C12N 5/10* (2006.01)
*C07H 21/04* (2006.01)

(52) U.S. Cl. ..... 800/298; 800/281; 435/410; 435/320.1; 536/23.2

(58) Field of Classification Search ........................ None
See application file for complete search history.

(56) References Cited

U.S. PATENT DOCUMENTS
6,479,070 B1   11/2002   Cain et al.

FOREIGN PATENT DOCUMENTS
| JP | 2001-158737 | 6/2001 |
| WO | WO 99/33958 | 7/1999 |
| WO | WO 00/20603 | 4/2000 |
| WO | WO 0138484 A2 * | 5/2001 |
| WO | WO 02/026946 A3 | 4/2002 |

OTHER PUBLICATIONS

Sequence alignment of SEQ ID No: 2 with Sequence Accession AAH50959, Lerchl et al, Aug. 28, 2001.*

Sequence alignment of SEQ ID No: 1 with Sequence Accession AV644153, Asamizu et al, Dec. 15, 2000.*
Hong et al., "Isolation and Characterization of a Δ5 FA Desaturase from *Pythium irregulare* by Heterologous Expression in *Saccharomyces cerevisiae* and Oilseed Crops," Lipids, vol. 37, No. 9, (2002), pp. 863-868.
Kajikawa et al., "Isolation and characterization of Δ6-desaturase, an ELO-like enzyme and Δ5-desaturase from the liverwort *Marchantia polymorpha* and production of arachidonic and eicosapentaenoic acids in the methylotrophic yeast *Pichia pastoris*," Plant Molecular Biology, 54, pp. 335-352, 2004.
International Search Report mailed on Oct. 18, 2005 in International PCT Application No. PCT/JP2005/013200 filed Jul. 11, 2005.
Masataka Kajikawa et al., "Ryokuso Chlamydomonas no Pinolenic Acid Namagosei o Ninau ω13 Fuhowaka Koso Idenshi no Tanri to Kino Kaiseki", Annual Meeting of the Molecular Biology Society of Japan Program Koen Yoshishu, Dec. 2004, vol. 27, p. 850 3PA-163.
Christian Giroud et al., "Lipids of *Chlamydomonas reinhardtii*. Incorporation of [$^{14}$C]Acetate, [$^{14}$C]Palmitate and [$^{14}$C]Oleate into Different Lipids and Evidence for Lipid-Linked Desaturation of Fatty Acids." *Plant Cell Physiology.* 1989, vol. 30, No. 1, pp. 121-128.
Christian Giroud et al. Lipids of *Chlamydomonas reinhardtii.* Analysis of Molecular Species and Intracellular Site(s) of Biosynthesis. *Plant Cell Physiology.* 1988, vol. 29, No. 4, pp. 587-595.
Asamizu et al., "Generation of Expressed Sequences Tags from Low-$CO_2$ and High-$CO_2$ Adapted Cells of *Chlamydomonos reinhardtii*," DNA Research, vol. 7, 2000, pp. 305-307, Kazusa DNA Research, Tokyo, Japan.
Grenier et al., Modification of the membrane fatty acid composition of *Chlamydomonas reinhardtii* cultured in the presence of liposomes, Plant Physiol. vol. 29, No. 5, 1991, pp. 429-440, Japanese Society of Plant Physiologists, Kyoto, Japan.
Domergue et al., "Cloning and functional characterization of *Phaeodactylum triconutum* front-end desaturases involved in eicosapentaenoic acid biosynthesis," Eur. J. Biochem., vol. 269, 2002, Feb. 2002, Blackwell Science, Berlin, Germany.
European Search Report mailed on Apr. 28, 2008, in European PCT Application No. 05766483.1 dated Apr. 15, 2008.
Wolff et al., "*Fokienia hodginsii* seed oil, another source of all-*cis* 5,9,12,15-18:4 (coniferonic) acid," Journal of American Oil Chemists' Society, vol. 76, No. 4, pp. 535-536, Apr. 1999.

* cited by examiner

*Primary Examiner* — Elizabeth F McElwain
(74) *Attorney, Agent, or Firm* — Drinker Biddle & Reath LLP

(57) ABSTRACT

The present invention relates to a polypeptide having a Δ5 fatty acid desaturation activity and a polynucleotide encoding the polypeptide as well as use thereof. For example, the present invention relates to a polypeptide, comprising (a) the amino acid sequence represented by SEQ ID NO: 2; or (b) the amino acid sequence in which one or more amino acids are substituted, deleted, inserted or added in the amino acid sequence represented by SEQ ID NO: 2, and having the Δ5 fatty acid desaturation activity; an antibody capable of binding to this polypeptide; a polynucleotide encoding the polypeptide; a vector comprising this polynucleotide; a cell or transformant introduced with the polynucleotide; a method of producing a fatty acid using the cell, and so on.

17 Claims, 5 Drawing Sheets

FIG. 3

```
CrDES5    ------------------------------MCRPTDSDSGPALPSIPHQVWI-IHGATYDLASYIKSHPGGDEAILLGRGRDCTELFEQYH
MaDES5    ------------------------------MGTDQGKTFTWEELA.HNTKGDLFLA.R.RV..VTKFLSR....VDTL...A...V.PV..M..
MpDES5    MPPHAPDSTGLGPEVFRLPDDAIPAQDRRSTQKKYSLSDVSKHNTPNDC.LV.W.KV...VT.WV.V....S-L.FVKA.Q.S.Q..DS..
PtDES5    -------MAPDADKLRQRQTTAVAKHNAATISTQERLCS.S.LKGEEVC.D.II...Q..-FD...E-T.KMFG.N.V.VQYKMI.
                                                      *              *    ****        *  *     *

CrDES5    VLNNKHLRVLERFRVTLPAAKVATNNLKEDMVSTISAFEGEEADAAAVVGIQQPAAPARVAHQSDPPYEDIKAMVRAHGNTKMSAPFVIL
MaDES5    AFGAADAIMKKYYVG..VSNELPVFP-------EPTVFHKTIKTR.E.YFTDRDIDPKNRPEI---------------WGRYALIFGSLI
MpDES5    P.YVRK.LAQFCIGELQTS.GDEKFKSSTLEYAGEHEVFYHTLKQR.ETYFRKQKINPRY.PQM---------------LVKSAVIGTL.
PtDES5    PYHTEKHLEKMKRVGKVT---------D.VC..YKFDTEF EREIKREVFKI.RRGK.---------------FG.LGWFFRAFC

CrDES5    HCLHVGLIWSMKLWWQGAFISAFIIPYFLWVLCAAMV EDGGH FAHSKRPLVNKLLTHTGALFT-NSVGCWYLQ HNILHE SYTNLVGKDG
MaDES5    ASYYAQLFVPFVVERTWLQVFE.I.MGFACAQVGLNPL..AS..SVTHN.T.W.I.GA.HDF.NGA.YLV.MY..MLG..P..IA.A.P
MpDES5    L.YY---FGFFWSQNVLLSMFL.S.MGFCTAEVGMSIM...N.GSYTQST.LGYVMGA.LD.VG-A.SFM.RQ..VAG...F..IDHY.P
PtDES5    YIAIFFY.QYHWVTTG-TSWLL.VAYGISQAMIGMNVQ..AN.G.T.....W..DM.GLGADFIG-G.KWL.QE..WT--.A...HAEM.P

CrDES5    DLDSHHPYMRIHP-EQSMLPANIHHAVRPFSHLIMYNFAHIGLTMISPLSYFRGVAAQKKGTADAKQAQDAQTVAQYHSTVMLQLVTVGA
MaDES5    .VSTFE.DV.R-------IKPNQKWFVNHINQD.FVPFLY..LAFKVRIQDINILYFV.TNDAIRVNPISTWHTVMFWGGKAFF.WYRL
MpDES5    .IRVKD.DL.R-------VTSQQPRRW.HEYQHI.LGVLIY.VLALKSVLIDDFS.FFSGAIGPV.I..MTPLEMGVFWGGKVVYALYMF
PtDES5    .SFGAE.MLLFNDYPLDHPARTWL.RFQA.FYMPVLAGYWLSAVFNPQIIDLQQRG.LSV.IRLDNAFIHSRRKYAVFWRAVYIA.N.I.

CrDES5    FYITPFLRFDFSRALLLTLLPTFMMSVAFMVIAQVSHIQMDAEAPSADLEK------LHWARRMALTSVDYSQESTLWAYLTIGLNMQSL
MaDES5    IVPLQY--LPLGKV...FTVADMVS.YWLALTF.AN.VVEEVQM.LP.ENG---IIQKD..AMQVE.TQ..AHD.H..TSI.GS..Y.AV
MpDES5    LLPMMYGQYNILTFIG.YI.SQLVAGWTLALFF..A.VVD..VF.V.ETDGGKAKIPSG..EMQVR.TTNF.SR.MF.THISG...H.IE
PtDES5    PFY.NSGLEWSW.VFGNIM.MGVAE.L.LA.LFSL..NFES.DRDPTAPL.-KTGEPVD.FKTQVE..CT.G--GF.SGCF.G...F.VE

CrDES5    HHIVPGVSYSQLPRLYPAYRAICEKHGIKLLERRNLAHAFWTHLQTLWVLSKTHSFVEVARKLA------
MaDES5    ..LF.N..QHHY.DILAIIKNT.SEYKVPY.VKDTFWQ..AS..EH.R...GLRPKEE------------ (21%)
MpDES5    ..LF....CHVHY.SIQ.IVK.T.DEFNVPYTSYPTFWA.LRA.F.H.KNVGLQDGLRLDG--------- (20%)
PtDES5    ..LF.RM.SAWY.YIA.KV.E..A...VHYAYYPWIHQN.LSTVRYMHAAGTGANWRQM..ENPLTGRA  (18%)
```

POLYPEPTIDE HAVING Δ5 DESATURATING ACTIVITY, POLYNUCLEOTIDE CODING FOR THE POLYPEPTIDE, AND USE THEREOF

CROSS REFERENCE TO RELATED APPLICATIONS

This application is the National Stage of International Application No. PCT/JP2005/013200, filed Jul. 11, 2005, and claims benefit of Japanese Application Nos. 2004-205325, filed Jul. 12, 2004, and 2005-044129, filed Feb. 21, 2005, all of which are incorporated herein in their entirety.

REFERENCE TO A SEQUENCE LISTING

A sequence listing containing SEQ ID NOS: 1-8 is incorporated herein by reference.

TECHNICAL FIELD

The present invention relates to a polypeptide having a Δ5 fatty acid desaturation activity, which catalyzes the synthesis of fatty acids such as pinolenic acid, etc., and a polynucleotide encoding the polypeptide, as well as representative use thereof.

BACKGROUND ART

Linoleic acid is a fatty acid which is effective for the prevention of arteriosclerosis and has an activity of lowering a serum cholesterol level. Linoleic acid is found in the particular species of microorganisms, plants or animals. However, higher animals lack desaturases needed to synthesize linoleic acid so that linoleic acid must be obtained from the diet (vegetable dietary sources).

Linoleic acid is metabolized in vivo to prostaglandins via arachidonic acid. In recent years, intake of a food with a high linoleic acid content such as egg or liver increases. It is pointed out, however, that excessive intake of linoleic acid may imbalance the synthesis of prostaglandins to cause allergic disease, etc.

Pinolenic acid, which is synthesized from linoleic acid, is a Δ5 desaturated fatty acid of 18 carbon atoms having 3 double bonds in one molecule (18:3Δ5,9,12). Since pinolenic acid cannot be metabolized to arachidonic acid in human, it is considered that prostaglandin metabolism is less affected by dietary intake. Also, pinolenic acid has an anticholesteremic activity (see, e.g., Br. J. Nutr., 72, p 775, 1994 [Nonpatent Literature 1]). Based on these findings, dietary oil rich in pinolenic acid, not linoleic acid, is widely marketed as a health food. Besides, fatty acids are used as raw materials to manufacture detergents or biodegradable plastics. Accordingly, pinolenic acid has been a focus of attention also as raw materials for industrial products.

Pinolenic acid is contained in gymnosperms such as pine, etc., and extracted and purified mainly from pine seeds (see, e.g., Eur. J. Lipid Sci. Technol. 104, p 234, 2002 [Nonpatent Literature 2]). However, problems of pine-derived pinolenic acid are pointed out that production costs are high and/or the supply of pines is limited in forest resources, and so on.

Pinolenic acid is considered to be biosynthesized from linoleic acid by the Δ5 desaturation reaction (see, e.g., Nonpatent Literature 2). This reaction is catalyzed by a Δ5 desaturation enzyme (hereinafter abbreviated as "Δ5 desaturase"). Most Δ5 desaturases isolated and identified to date participate in the Δ5 desaturation reaction for converting di-homo-γ-linolenic acid (DGLA, 20:3Δ8,11,14) into arachidonic acid (AA, 20:4Δ5,8,11,14), or eicosatetraenoic acid (ETA, 20:4Δ8,11,14,17) into eicosapentaenoic acid (EPA, 20:4Δ5, 8,11,14,17). These enzymes are termed front-end desaturases since they introduce a new double bond at a site most proximal to the carboxyl end than any of the double bonds the substrate fatty acid has (see, e.g., Curr. Opin. Plant Biol. 2, p 123, 1999 [Nonpatent Literature 3]).

Δ5 Desaturase genes that chiefly govern the biosynthesis of polyunsaturated fatty acids having 20 carbon atoms such as AA-EPA, etc. are isolated from filamentous fungi (*Mortierella alpina, Pythium irregulare*), *Thraustochytrium* sp., *Phaeodactylum tricornutum, Caenorhabditis elegans*, rat, human, *Physcomitrella patens, Marchantia polymorpha*, etc., all of which have the cytochrome b5 domain at the N-terminus (see, e.g., J. Biol. Chem., 273, p 19055, 1998 [Nonpatent Literature 4]), J. Biol. Chem., 273, p 29360, 1998 [Nonpatent Literature 5], Eur. J. Biochem. 269, p 4105, 2002 [Nonpatent Literature 6], FEBS Lett. 439, p 215, 1998 [Nonpatent Literature 7], Arch. Biochem. Biophys., 391, p 8, 2001 [Nonpatent Literature 8], J. Biol. Chem., 274, p 37335, 1999 [Nonpatent Literature 9], J. Biol. Chem., 278, p 35115, 2003 [Nonpatent Literature 10], Plant Mol. Biol., http://ipsapp008.kluweronline.com/IPS/content/ext/x/J/5082/I/124/A/4/type/PDF/article.htm [Nonpatent Literature 11], and J. Biol. Chem. 276, p 31561, 2001 [Nonpatent Literature 12], Lipids, 37, p 863, 2002 [Nonpatent Literature 13], but the sequence of Δ5 desaturase gene for *Physcomitrella patens* is not published). Also, Δ5 desaturase genes involved in the desaturation of saturated fatty acids or monoenoic acids of 16-20 carbon atoms have been isolated from cellular slime mold *Dictyostelium discoideum, Bacillus subtilis*, and oil plant meadowfoam (see, e.g., Eur. J. Biochem., 265, 809, 2002 [Nonpatent Literature 14], Eur. J. Biochem., 267, 1813-1818, 2000 [Nonpatent Literature 15], J. Bacteriol., 185, 3228-3231, 2003 [Nonpatent Literature 16], Plant Physiol., 124, 243-251, 2000 [Nonpatent Literature 17]).

DISCLOSURE OF THE INVENTION

Pinolenic acid has such a peculiar physical property as having multiple double bonds in the molecule. If its production costs can be reduced, pinolenic acid will also be industrially available as industrial sources (raw materials of industrial products such as films, biodegradable plastics, functional fibers, lubricant oil or detergents). As described above, however, the production of pinolenic acid is relied on the extraction from pine tree seeds and involves problems that pinolenic acid cannot be mass-produced, thus leading to high production costs, pine trees as a source of supplying pinolenic acid are limited in forest resources, and so on. If pinolenic acid can be mass-produced by genetic engineering technology or the like, it will enable to use pinolenic acid at low costs as a versatile raw material.

In view of the problems described above, the present invention has been made and its object is to produce pinolenic acid using living modified organisms having introduced therein a polynucleotide encoding the polypeptide involved in pinolenic acid synthesis to put into practice a low cost and environmentally benign production process for pinolenic acid.

The polypeptide in accordance with the present invention is a polypeptide having the Δ5 fatty acid desaturation activity, which comprises (a) the amino acid sequence represented by SEQ ID NO: 2; or (b) an amino acid sequence in which one or more amino acids are substituted, deleted, inserted or added in the amino acid sequence represented by SEQ ID NO: 2.

According to the feature described above, the polypeptide in accordance with the present invention can catalyze the Δ5 desaturated fatty acid synthesis reaction.

The antibody in accordance with the present invention is also characterized by binding to the polypeptide described above.

According to the feature described above, the antibody in accordance with the present invention can identify the organism which expresses the polypeptide having the Δ5 fatty acid desaturation activity, its tissues or cells.

The polynucleotide in accordance with the present invention is further characterized by encoding the polypeptide described above.

The polynucleotide in accordance with the present invention is preferably a polynucleotide, which is either (a) or (b) described below:
  (a) the polynucleotide consisting of the base sequence represented by SEQ ID NO: 1; or,
  (b) the polynucleotide hybridizable to (i) or (ii) below under stringent conditions:
    (i) the polynucleotide consisting of the base sequence represented by SEQ ID NO: 1; or,
    (ii) the polynucleotide consisting of a base sequence complementary to the base sequence represented by SEQ ID NO: 1.

Furthermore, the polynucleotide in accordance with the present invention is preferably a polynucleotide, which is either (a) or (b) described below:
  (a) the polynucleotide consisting of the 68th-1498th base sequence in the base sequence represented by SEQ ID NO: 1; or,
  (b) the polynucleotide hybridizable to either (i) or (ii) below under stringent conditions:
    (i) the polynucleotide consisting of the 68th-1498th base sequence in the base sequence represented by SEQ ID NO: 1; or,
    (ii) the polynucleotide consisting of a base sequence complementary to the 68th-1498th base sequence in the base sequence represented by SEQ ID NO: 1.

In the feature described above, the aforesaid polynucleotide can be used to synthesize the polypeptide having the Δ5 fatty acid desaturation activity in transformants or cells.

Also, the oligonucleotide in accordance with the present invention is characterized in that it is a fragment of the polynucleotide described above.

Preferably, the oligonucleotide in accordance with the present invention consists of the base sequence represented by SEQ ID NO: 5 or 6.

In the feature described above, the aforesaid oligonucleotide can be used as a hybridization probe for detecting the polynucleotide encoding the polypeptide having the Δ5 fatty acid desaturation activity or as a primer for amplifying the said polynucleotide. In addition, by using the oligonucleotide described above, the organism which expresses the polypeptide having the Δ5 fatty acid desaturation activity, or its tissues or cells can be identified. Moreover, by using the aforesaid oligonucleotide as an antisense oligonucleotide, expression of the polypeptide having the Δ5 fatty acid desaturation activity can be controlled in the organism or its tissues or cells.

The vector in accordance with the present invention is characterized by comprising the polynucleotide described above.

In the feature described above, the polypeptide having the Δ5 fatty acid desaturation activity can be expressed by introducing the polynucleotide into organisms or cells, or the polypeptide having the Δ5 fatty acid desaturation activity can be synthesized by using a cell-free protein synthesis system.

In the method of producing the polypeptide in accordance with the present invention, it is preferred to use the vector described above.

The transformant in accordance with the present invention is characterized in that the polynucleotide described above is introduced.

In the transformant in accordance with the present invention, preferably the fatty acid composition is modified.

In addition, the transformant described above is preferably an organism or its progeny, or tissues derived therefrom.

The organism described above is preferably a plant or its progeny, or tissues derived therefrom.

Further when the organism described above contains linolenic acid, pinolenic acid can be produced by introducing the gene therein, irrespective of the species of organism. Examples of the plant include, but not are limited to, tobacco plant, rice plant and tomato.

The method of producing the polypeptide in accordance with the present invention is characterized by using the transformant described above.

In the feature described above, the polypeptide which catalyzes the Δ5 fatty acid desaturation reaction can be provided at low costs under environment-friendly conditions.

The method of producing the fatty acid in accordance with the present invention is characterized by using the transformant described above.

The fatty acid is preferably pinolenic acid or coniferonic acid.

The cell in accordance with the present invention is characterized by comprising the vector described above.

The cell described above is preferably a cell from rice plant, tobacco plant, tomato or yeast.

In the feature described above, the cell which can provide the Δ5 fatty acid desaturation reaction-catalyzing polypeptide at low costs under environment-friendly conditions.

The method of producing the polypeptide in accordance with the present invention is characterized by using the cell described above.

According to the feature described above, the polypeptide which catalyzes the Δ5 fatty acid desaturation reaction can be readily produced.

The method of producing the fatty acid in accordance with the present invention is characterized by using the cell described above.

The food or industrial product in accordance with the present invention is characterized in comprising pinolenic acid or coniferonic acid obtained by the method of producing the fatty acid described above.

The detector in accordance with the present invention is characterized by immobilizing the polynucleotide and/or oligonucleotide described above on a substrate.

In the feature described above, the organism which expresses the polypeptide having the Δ5 fatty acid desaturation activity can be readily detected by detecting the polynucleotide which hybridizes to the polynucleotide or oligonucleotide described above.

The detector in accordance with the present invention is characterized by immobilizing the polypeptide described above on a substrate.

In the feature described above, a substance which regulates the Δ5 fatty acid desaturation activity of the polypeptide described above can be readily detected by detecting the substance which interacts with the polypeptide described above.

The detector in accordance with the present invention is characterized in immobilizing the antibody described above on a substrate.

According to the feature described above, the polypeptide having the Δ5 fatty acid desaturation activity can be readily detected by detecting an antibody capable of binding to the antibody described above.

The polypeptide in accordance with the present invention is capable of catalyzing the desaturation reaction of endogenous linoleic acid in organisms such as plants, etc. Accordingly, fatty acids such as pinolenic acid, etc. can be produced in a large scale at a low cost and environment-friendly production process by using the transformant or cell wherein a recombinant expression vector comprising the polynucleotide encoding the polypeptide in accordance with the present invention. Furthermore, the present invention can provide inexpensive foods or industry products through the large scale production of pinolenic acid.

BRIEF DESCRIPTION OF THE DRAWINGS

FIG. 3 shows the alignment in comparison of the amino acid sequence of the C. reinhardtii Δ5 desaturase (CrDES5) with the amino acid sequences of Δ5 desaturases for M. alpina (MaDES5), M. polymorpha (MpDES5) and P. tricomutum (PtDES5).

BEST MODE FOR CARRYING OUT THE INVENTION

Figure 1:
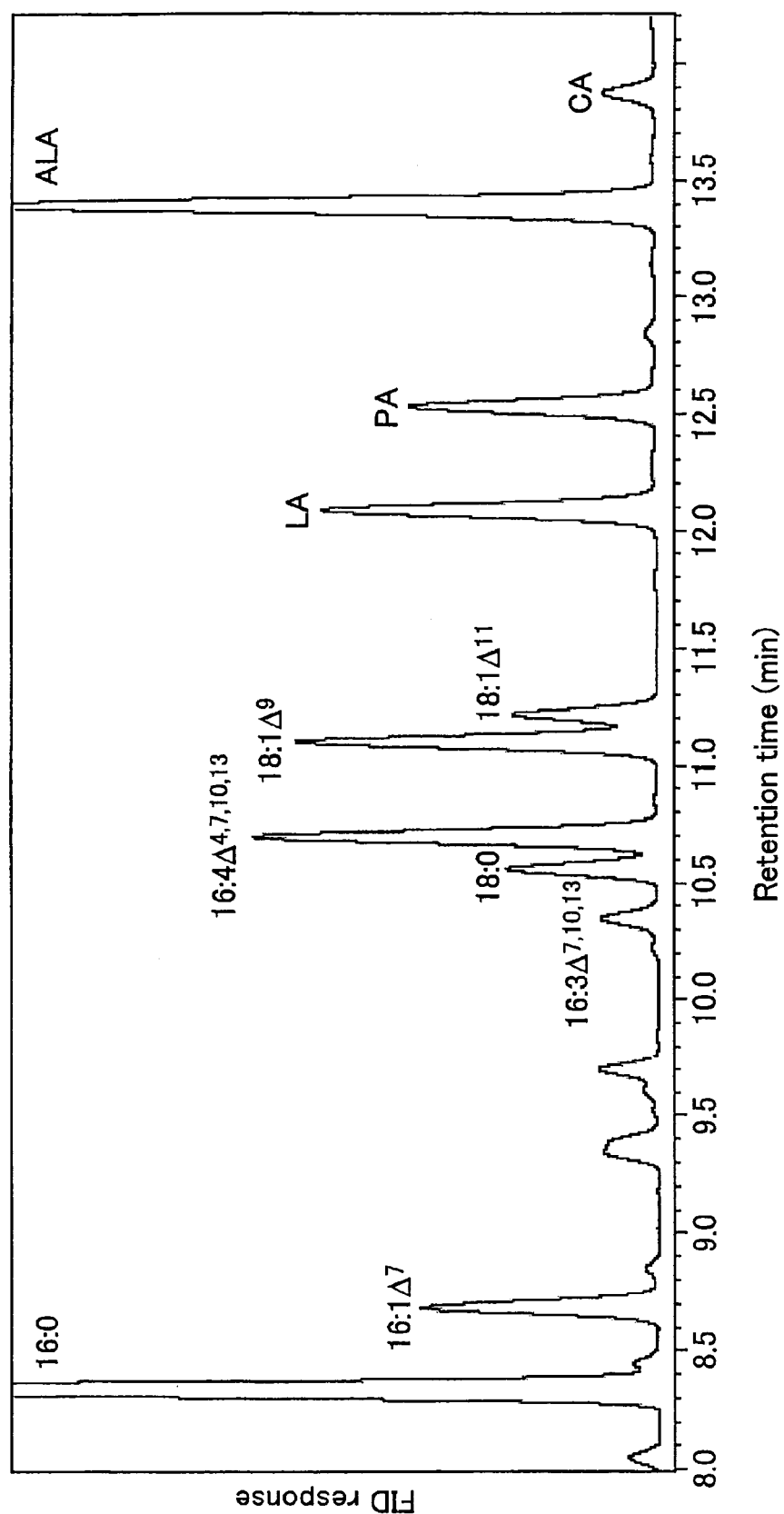
FIG. 1 shows the results of GC analysis of fatty acid methyl esters for C. reinhardtii.

Hereinafter, the polypeptide in accordance with the present invention having the Δ5 fatty acid desaturation activity and the polynucleotide encoding the polypeptide as well as use thereof are described in detail.

(1) Polypeptide

The present inventors have found that a polypeptide encoded by the polynucleotide isolated from *Chlamydomonas* is a novel Δ5 desaturase, which main substrate is linoleic acid and α-linolenic acid, and have thus come to accomplish the present invention.

The polypeptide in accordance with the present invention is a novel Δ5 desaturase and Δ5-desaturates linoleic acid in methylotrophic yeast at a very high efficacy (approximately 80%) to produce pinolenic acid.

Throughout the specification, the term "polypeptide" is interchangeably used with "peptide" or "protein." A "fragment" of the polypeptide is intended to mean the partial piece of the polypeptide. The polypeptide in accordance with the present invention may be isolated from naturally occurring resources or may also be chemically synthesized.

The term "isolated" polypeptide or protein is intended to mean the polypeptide or protein isolated from its natural environment. For example, the polypeptide or protein, which is expressed, recombined and produced in host cells, is considered to be isolated as done in naturally occurring or recombinant polypeptide or protein substantially purified by means of optional adequate techniques.

The polypeptide in accordance with the present invention includes purified natural products, chemically synthesized products and products produced from prokaryotic hosts or eukaryotic hosts (including, e.g., bacterial cells, yeast cells, higher plant cells, insect cells and mammalian cells) by recombinant technology. The polypeptide in accordance with the present invention can be glycosylated or non-glycosylated, depending upon host used in the recombinant production procedure. Furthermore, the polypeptide in accordance with the present invention may include initial modified methionine residues as a result of host-mediated process in some cases.

The present invention provides the polypeptide having the Δ5 fatty acid desaturation activity. In one embodiment, the polypeptide in accordance with the present invention is the polypeptide comprising the amino acid sequence represented by SEQ ID NO: 2, or variants of the polypeptide comprising the amino acid sequence represented by SEQ ID NO: 2 and having the Δ5 fatty acid desaturation activity.

Such variants include those produced by deletions, insertions, inversions, duplications and type substitutions (for example, substituting one hydrophilic residue with another, but normally not substituting strongly hydrophilic residues with strongly hydrophobic residues). In particular, "neutral" amino acid substitutions in the polypeptide will generally have little effect on activity of the polypeptide.

It is well known in the art that some amino acid sequences of the polypeptide can be varied without significant effect on the structure or function of the polypeptide. It is also well known that in naturally occurring proteins, variants in which the structure or function of the protein is not modified significantly, are present.

One skilled in the art can easily mutate one or more amino acids in the amino acid sequence of the polypeptide using techniques well known. For example, optional bases of the polynucleotide encoding the polypeptide can be mutated according to the point mutation process publicly known. Also, primers corresponding to optional sites in the polynucleotide encoding the polypeptide can be designed to prepare deleted variants or added variants. In addition, it can be easily determined by the method described herein whether the variants prepared have a desired activity or not.

Preferred variants have conservative or non-conservative amino acid substitutions, deletions or additions. Preferred are silent substitutions, additions and deletions, and more preferred are conservative substitutions. These variants do not alter the activities of the polypeptide in accordance with the present invention.

Typically considered as conservative substitutions are replacements of one amino acid with another in the aliphatic amino acids Ala, Val, Leu and Ile; interchange of the hydroxyl residues Ser and Thr, interchange of the acidic residues Asp and Glu, substitution between the amide residues Asn and Gln, interchange of the basic residues Lys and Arg and substitution between the aromatic residues Phe and Tyr.

As described above in detail, further guidance concerning which amino acid changes are likely to be phenotypically silent (i.e., are unlikely to have significantly deleterious effects on the function) can be found in Bowie, J. U., et al., "Deciphering the Message in Protein Sequences: Tolerance to Amino Acid Substitutions," Science 247: 1306-1310 (1990) (which is hereby incorporated by reference).

The polypeptide in accordance with the present invention is the polypeptide having the Δ5 fatty acid desaturation activity, which comprises:

(a) the amino acid sequence represented by SEQ ID NO: 2; or (b) the amino acid sequence in which one or more amino acids are substituted, deleted, inserted or added in the amino acid sequence represented by SEQ ID NO: 2.

The term "one or more amino acids are substituted, deleted, inserted or added" described above is used to mean substitutions, deletions, insertions or additions (or combination thereof) of amino acids of the number to such an extent that can be replaced, deleted, inserted and/or added (preferably 1 to 10, more preferably 1 to 7, much more preferably 1 to several (e. g., 5) and most preferably 1 to 2), by publicly known variant polypeptide production processes such as the site-directed mutagenesis, etc. As described above, these variant polypeptides are not limited to polypeptides having artificially induced variations by publicly known variant polypeptide production processes but may also include those isolated and purified from naturally occurring polypeptides.

The polypeptide in accordance with the present invention includes, but is not limited to, polypeptides wherein the amino acids are linked through peptide bonds, and may also be conjugated polypeptides having a structure other than the polypeptide. As used herein, the "structure other than the polypeptide" includes, but is not particularly limited to, a sugar chain, an isoprenoid group, etc.

The polypeptide in accordance with the present invention may include additional polypeptides. The additional polypeptides include polypeptides tagged with an epitope such as His, Myc, Flag, etc.

Also, the polypeptide in accordance with the present invention may be in such a state that the polynucleotide in accordance with the present invention (the gene encoding the polypeptide in accordance with the present invention) is introduced into the host cell and its polypeptide is intracellularly expressed, or may be isolated and purified from cells, tissues, etc. Alternatively, the polypeptide in accordance with the present invention may also be chemically synthesized.

In another embodiment, the polypeptide in accordance with the present invention may be expressed in a modified form, such as a fusion protein. For example, a region of additional amino acids, charged amino acids especially, of the polypeptide in accordance with the present invention may be added to the N-terminus of the polypeptide to improve the stability and persistence in the host cell during purification or during subsequent handling and storage.

The polypeptide in accordance with this embodiment can be added to, e.g., a tag marker (a tag sequence or a marker sequence) at the N-terminus or C-terminus, which is a sequence encoding the peptide to facilitate purification of a fused polypeptide. Such sequences can be removed prior to final preparation of the polypeptide. In a certain preferred embodiment of this aspect of the present invention, the tag amino acid sequence is hexahistidine peptide (the tag supplied by a pQE vector (Qiagen, Inc.), among others, many of them are available publicly and/or commercially. As described in, e.g., Gentz, et al., Proc. Natl. Acad. Sci. USA 86:821-824 (1989) (which is hereby incorporated by reference), hexahistidine provides convenient purification for a fusion protein. The "HA" tag is another peptide useful for purification, which corresponds to the epitope derived from the influenza hemagglutinin (HA) protein, described by Wilson et al., Cell 37: 767 (1984) (which is hereby incorporated by reference). Other such fusion proteins include the polypeptide in accordance with this embodiment, which is fused to Fc at the N- or C-terminus, or its fragments.

In yet another embodiment, the polypeptide in accordance with the present invention may be recombinantly produced or chemically synthesized, as will be described below in detail.

Recombinant production can be carried out by using techniques well known in the art, and can be performed using, for example, such vectors and cells as described below in detail.

Synthetic peptides can be synthesized by using the methods publicly known. For example, Houghten describes a simple method for synthesis of large numbers of peptides, such as 10-20 mg of 248 different 13-residue peptides representing single amino acid variants of a segment of the HA1 polypeptide, which are prepared and characterized in less than 4 weeks; Houghten, R. A., Proc. Natl. Acad. Sci. USA 82:5131-5135 (1985). This "Simultaneous Multiple Peptide Synthesis (SMPS)" process is further described in U.S. Pat. No. 4,631,211 issued to Houghten et al. (1986). According to this procedure, the individual resins for the solid-phase synthesis of various peptides are contained in separate solvent-permeable packets, which enable the optimal use of the many identical repetitive steps involved in solid-phase methods. A completely manual procedure allows 500-1000 or more syntheses to be conducted simultaneously (Houghten et al., supra, 5134). These literatures are hereby incorporated by reference.

The polypeptide in accordance with the present invention is useful in the method for Δ5 desaturation of linoleic acid to produce pinolenic acid and in the kit therefor, as described below in detail.

The present inventors have found that the polypeptide in accordance with the present invention Δ5-desaturates not only linoleic acid but also α-linolenic acid to produce coniferonic acid (in yield of, e.g., 60%).

α-Linolenic acid is an unsaturated fatty acid of 18 carbon atoms and three double bonds in one molecule (18:3Δ9,12,15), and is a precursor of prostaglandins formed from eicosapentaenoic acid (EPA). The higher animals have lost the ability to synthesize α-linolenic acid as in the case of linoleic acid, and hence ingest α-linolenic acid from their diet (vegetable food). Coniferonic acid is formed by Δ5 desaturation of α-linolenic acid, but its utility has not yet been reported.

The present inventors have further found that the polypeptide in accordance with the present invention not only has the ability of Δ5-desaturating linoleic acid and/or α-linolenic acid but also has the Δ7 desaturation activity on a dienoic acid (20:2Δ11,14) and trienoic acid (20:3Δ11,14,17) of 20 carbon atoms, respectively.

As described above, the polypeptide in accordance with the present invention has the activity of Δ5-desaturating linoleic acid and/or α-linolenic acid but also the activity of Δ7-desaturating dienoic acids (20:2Δ11,14) and trienoic acids (20:3Δ11,14,17) of 20 carbon atoms, respectively. Using the polypeptide in accordance with the present invention having these activities, plants species abundant in linoleic acid but deficient in α-linolenic acid can be chosen as those capable of expressing the polypeptide in accordance with the present invention. Rice oil is an example of plant oils having such a fatty acid composition and a rice plant is considered to be a promising target plant for producing pinolenic acid. Other typical oil crops include soybean, rapeseed, sesame, palm, cotton, etc. are. Also, linoleic acid is widely distributed in cell membranes or seed storage lipids of plants, examples of which include rice plant, barley, wheat, potato, tomato, poplar, banana, eucalyptus, sweet potato, alfalfa, lupine, flax, kidney bean, lettuce, radish, sweet corn, cauliflower, rose, chrysanthemum, carnation, snapdragon, cyclamen, orchid, prairie gentian, freesia, gerbera, gladiolus, babys-breath, kalanchoe, pelargonium, geranium, petunia, torenia, tulip, etc.

For instance, methods for transformation of rice plants which can be used include those described in the literature publicly known (A Protocol Book for Model Plant Species, Shujunsha Publishing Co., 1996).

As described above, it is sufficient for the polypeptide in accordance with the present invention to contain at least the amino acid sequence represented by SEQ ID NO: 2. It should thus be noted that the polypeptides comprising the amino acid sequence represented by SEQ ID NO: 2 and optional amino acid sequences having specific functions (e.g., a tag) are included within the present invention. Furthermore, the amino acid sequence represented by SEQ ID NO: 2 and the optional amino acid sequences may be linked via appropriate linker peptides in such a way that the respective functions are not inhibited.

Also, the polypeptide in accordance with the present invention has the Δ5 desaturation activity on α-linolenic acid and the Δ7 desaturation activity on the dienoic acids or trienoic acids having 20 carbon atoms, in addition to the Δ5 desaturation activity of the polypeptide on linoleic acid. Accordingly, the use of the polypeptide should not be limited only to the Δ5 desaturation of linoleic acid to produce pinolenic acid.

In other words, an object of the present invention is to provide the polypeptide, which has the Δ5 desaturation activity exclusively on linoleic acid or ALA without any contribution to the biosynthesis of AA/EPA, but does not reside in the methods of producing polypeptides specifically described in the present invention, and so on. It should thus be noted that such polypeptides that have the activity of Δ5 desaturating linoleic acid produced by these methods are deemed to be within the technical scope of the present invention.

(2) Polynucleotide

The present invention provides the polynucleotide encoding the polypeptide in accordance with the present invention having the Δ5 fatty acid desaturation activity. As used herein, the term "polynucleotide" refers interchangeably to "nucleic acid" or "nucleic acid molecule," and is intended to mean the polymeric form of nucleotides. The term "base sequence" as used herein refers interchangeably to "nucleic acid sequence" or "nucleotide sequence," and is given as the sequence of deoxyribonucleotides (abbreviated as A, G, C and T). Also, the "polynucleotide comprising the base sequence represented by SEQ ID NO: 24 or a fragment thereof" is intended to mean the polynucleotide comprising the sequences given by the respective deoxynuclotides A, G, C and/or T represented by SEQ ID NO: 24, or fragmental parts thereof.

The polynucleotide in accordance with the present invention can be present in the form of RNA (e.g., mRNA) or DNA (e.g., cDNA or genomic DNA). The DNA may be double-stranded or single-stranded. Single-stranded DNA or RNA may be the coding strand (also known as the sense strand), or it may be the non-coding strand (also known as the anti-sense strand).

The term "oligonucleotide" as used herein is intended to mean linked nucleotides of, e.g., 2 to 100 (e.g. several to several tens) and refers interchangeably to "polynucleotide." In the oligonucleotides, a short string of nucleotides are called a dinucleotide (dimer) or a trinucleotide (trimer), and a long string of nucleotides are expressed by the number of nucleotides polymerized, such as a 30-mer or a 100-mer. The oligonucleotide may be produced as a fragment of longer polynucleotide or chemically synthesized.

The fragment of the polynucleotide in accordance with the present invention is intended to mean the fragment of at least 12 nt (nucleotides), preferably about 15 nt, more preferably 20 nt, much more preferably about 30 nt and most preferably about 40 nt, in length. For example, a fragment containing 20 or more bases from the base sequence represented by SEQ ID NO: 2 is intended to be meant by the fragment of at least 20 nt in length. By referring to the specification, one skilled in the art can readily produce a DNA fragment based on SEQ ID NO: 2, since the base sequence represented by SEQ ID NO: 2 is provided. For instance, digestion with a restricted endonuclease or ultrasonic shear is readily available for preparing fragments with various sizes. Alternatively, such fragments can be prepared synthetically. Appropriate fragments (oligonucleotides) are synthesized on an Applied Biosystems Incorporated (ABI, 850 Lincoln Center Dr., Foster City, Calif. 94404) Model 392 synthesizer, etc.

Also, the polynucleotide in accordance with the present invention can be fused to the polynucleotide encoding the aforesaid tag marker (tag sequence or marker sequence) at the 5' or 3' end.

The present invention further relates to variants of the polynucleotide encoding the polypeptide having the Δ5 fatty acid desaturation activity. Variants may occur spontaneously, such as a naturally occurring allelic variant. By the "allelic variant" it is intended to mean one of several alternate forms of a gene occupying a given locus on a chromosome of an organism. Non-naturally occurring variants may be produced by using mutagenesis techniques well known in the art.

Such variants include those produced by deletions, substitutions or additions, which may involve one or more bases in the base sequences of the polynucleotide encoding the polypeptide having the Δ5 fatty acid desaturation activity. The variants may be altered in coding regions, non-coding regions, or both regions. Alterations in the coding regions may produce conservative or non-conservative amino acid substitutions, deletions or additions.

The present invention further provides the isolated polynucleotide comprising the polynucleotide encoding the polypeptide, which has the Δ5 fatty acid desaturation activity, or the polynucleotide, which hybridizes to said polynucleotide, under stringent hybridization conditions.

In one embodiment, the polynucleotide in accordance with the present invention is the polynucleotide encoding the polypeptide having the Δ5 fatty acid desaturation activity, and is preferably any polynucleotide encoding (a) the polypeptide consisting of the amino acid sequence represented by SEQ ID NO: 2; or (b) the polypeptide comprising the amino acid sequence wherein one or more amino acids are substituted, deleted, inserted or added in the amino acid sequence represented by SEQ ID NO: 2.

In another embodiment, the polynucleotide in accordance with the present invention is the polynucleotide encoding the polypeptide having the Δ5 fatty acid desaturation activity and is preferably any of the polynucleotides (a) and (b) below:

(a) the polynucleotide consisting of the base sequence represented by SEQ ID NO: 1; or, (b) the polynucleotide hybridizable to any one of (i) and (ii) below under stringent conditions:

(i) the polynucleotide consisting of the base sequence represented by SEQ ID NO: 1; or, (ii) the polynucleotide consisting of a base sequence complementary to the base sequence represented by SEQ ID NO: 1.

By the "stringent conditions" described above, it is intended to mean that hybridization occurs between sequences only when there is at least 90% identity, preferably at least 95% identity, and most preferably at least 97% identity therebetween.

The hybridization described above can be performed by such a well-known method as described in Sambrook et al., Molecular Cloning, A Laboratory Manual, 2nd Ed., Cold Spring Harbor Laboratory (1989). Higher temperature and lower salt concentration normally result in higher stringency (difficulty of hybridization) so that a more homologous polynucleotide can be acquired. For the hybridization conditions, heretofore known conditions can be advantageously used without any particular restrictions. The conditions include, for example, 42° C., 6×SSPE, 50% formamide, 1% SDS, 100 µg/ml salmon sperm DNA, 5×Denhardt's solution (wherein 1×SSPE; 0.18M sodium chloride, 10 mM sodium phosphate, pH 7.7, 1 mM EDTA, 5×Denhardt's solution; 0.1% bovine serum albumin, 0.1% phycoll, 0.1% polyvinylpyrrolidone).

In yet another embodiment, the polynucleotide in accordance with the present invention is the polynucleotide encoding the polypeptide having the Δ5 fatty acid desaturation activity, and is preferably either (a) or (b) below:

(a) the polynucleotide consisting of the 68th-1498th base sequence in the base sequence represented by SEQ ID NO: 1; or, (b) the polynucleotide hybridizable to either (i) or (ii) below under stringent conditions:

(i) the polynucleotide consisting of the 68th-1498th base sequence in the base sequence represented by SEQ ID NO: 1; or, (ii) the polynucleotide consisting of a base sequence complementary to the 68th-1498th base sequence in the base sequence represented by SEQ ID NO: 1.

In yet further embodiment, the polynucleotide in accordance with the present invention is preferably an oligonucleotide, which is a fragment of the polynucleotide described above, and most preferably the oligonucleotide consisting of the base sequence represented by SEQ ID NO: 5 or 6.

The polynucleotide or oligonucleotide in accordance with the present invention includes not only double-stranded DNA but single-stranded DNA or RNA such as sense strand and antisense strand, which construct the double-stranded DNA. The polynucleotide or oligonucleotide in accordance with the present invention can be used as a tool for gene expression manipulation via an antisense RNA mechanism. In its basic principle, antisense RNA technology involves the introduction of a chimeric gene which produces a RNA transcript complementary to the target gene. The resulting phenotype is a decrease in the gene product derived from the endogenous gene. By introducing the oligonucleotide in accordance with the present invention to reduce the level of the polypeptide having the Δ5 fatty acid desaturation activity, the pinolenic acid content in plant can be reduced. The DNA includes cDNA, genomic DNA, etc. which are produced by, for example, cloning, chemical synthesis technology or a combination thereof. The polynucleotide or oligonucleotide in accordance with the present invention may also be those having a sequence from the untranslated region (UTR), a sequence from vector sequences (including expression vector sequences), etc.

A method of obtaining the polynucleotide or oligonucleotide in accordance with the present invention includes a method using a publicly known technique, which comprises isolating a DNA fragment comprising the polynucleotide or oligonucleotide in accordance with the present invention and cloning the DNA fragment. For example, the probe which specifically hybridizes to a part of the base sequence of the polynucleotide in the present invention is prepared, followed by screening of a genomic DNA library or cDNA library. Such a probe may be the probe of any sequence and/or any length, so long as it is the probe that specifically hybridizes to at least a part of the base sequence of the polynucleotide in accordance with the present invention or its complementary sequence.

Alternatively, the method of obtaining the polynucleotide in accordance with the present invention further includes methods using amplification means such as PCR, etc. For example, the DNA fragment comprising the polynucleotide in accordance with the present invention can be obtained in large amounts by preparing primers from 5'-end and 3'-end sequences (or their complementary sequences), respectively, in cDNA of the polynucleotide in the present invention, conducting PCR, etc. using these primers on a template of genomic DNA (or cDNA), etc. to amplify the DNA region lying between the two primers.

Supply sources to acquire the polynucleotide in accordance with the present invention are not particularly limited but are preferably biological materials containing pinolenic acid and coniferonic acid, in addition to linoleic acid and α-linolenic acid. As used herein, the term "biological material" is intended to mean biological samples (tissue samples or a cell samples obtained from organisms). Since it is considered that pinolenic acid is produced from linoleic acid through the Δ5 desaturation reaction and coniferonic acid from α-linolenic acid through the Δ5 desaturation reaction, the polynucleotide encoding the polypeptide which catalyzes the synthesis reactions of pinolenic acid and coniferonic acid can be obtained, so long as the biological material contains these fatty acids. In EXAMPLES later described, C. reinhardtii belonging to the Chlamydomonadales is used but is not limited thereto.

As described above, the polypeptide encoded by the polynucleotide in accordance with the present invention has the activity of Δ5 desaturating linoleic acid; in addition, the polynucleotide also has the activity of Δ5 desaturating α-linolenic acid and the activity of Δ7 desaturating a dienoic acid or trienoic acid having 20 carbon atoms. Therefore, use of the polynucleotide in accordance with the present invention should not be limited only to the Δ5 desaturation of linoleic acid to produce pinolenic acid.

In other words, an object of the present invention is to provide the polynucleotide encoding the polypeptide having the activity of Δ5 desaturating linoleic acid and the oligonucleotide capable of hybridizing the polynucleotide, but not to provide methods of preparing the polynucleotide and oligonucleotide illustratively described herein. It should thus be noted that the polynucleotide encoding the polypeptide having the activity of Δ5 desaturating linoleic acid, which is obtained by any method other than those described above, are also deemed to be within the technical scope of the present invention.

(3) Antibody

The present invention provides an antibody capable of specifically binding to the polypeptide having the Δ5 fatty acid desaturation activity. As used herein, the term "antibody" is used to mean immunoglobulins (IgA, IgD, IgE, IgG, IgM and Fab fragments thereof, F(ab')$_2$ fragment and Fc fragment); examples include, but is not limited to, a polyclonal antibody, a monoclonal antibody, a single-chain antibody, an anti-idiotypic antibody and a humanized antibody. The antibody in accordance with the present invention may be useful for selecting biological materials which express the polypeptide having the Δ5 fatty acid desaturation activity.

The "antibody" can be produced according to various known methods (e.g., HarLow et al., "Antibodies: A laboratory manual, Cold Spring Harbor Laboratory, New York (1988)", Iwasaki et al., "Monoclonal Antibody Hybridoma and ELISA", published by Kodansha (1991)).

Peptide antibodies can be produced by methods well known in the art, for example, see Chow, M. et al., Proc. Natl. Acad. Sci. USA, 82: 910-914; and Bittle, F. J. et al., J. Gen.

Virol., 66: 2347-2354 (1985) (all are hereby incorporated by reference herein). In general, animals may be immunized with free peptide; however, anti-peptide antibody titer may be boosted by coupling of the peptide to a macromolecular carrier, (e.g., keyhole limpet hemacyanin (KLH) or tetanus toxoid). For example, cysteine-containing peptides may be coupled to a carrier using a linker such as m-maleimidobenzoyl-N-hydroxysuccinimide ester (MBS), while other peptides may be coupled to a carrier using a more general linking agent such as glutaraldehyde. Animals such as rabbits, rats and mice are immunized with either free or carrier-coupled peptides, e.g., by intraperitoneal and/or intradermal injection of emulsions containing about 100 µg of peptide or carrier protein and Freund's adjuvant. Several booster injections may be required, e.g., at intervals of about 2 weeks, to provide a useful titer of anti-peptide antibody which can be detected, e.g., by ELISA using a free peptide adsorbed to a solid surface. The titer of anti-peptide antibodies in serum from an immunized animal may be increased by selection of anti-peptide antibodies, e.g., by adsorption to the peptide on a solid support and elution of the selected antibodies according to methods well known in the art.

As used herein, the term "antibody capable of specifically binding to the polypeptide having the Δ5 fatty acid desaturation activity is meant to include complete antibody molecules and antibody fragments (e.g., Fab and F(ab')$_2$ fragments), which are capable of specifically binding to the polypeptide having the Δ5 fatty acid desaturation activity. Fab and F(ab')$_2$ fragments lack the Fc fragment of intact antibody, are removed more rapidly from the circulation, and may have less non-specific tissue binding of an intact antibody (Wahl et al., J. Nucl. Med. 24: 316-325 (1983) (which is hereby incorporated by reference)). Thus, these fragments are preferred.

In addition, an additional antibody capable of binding to the peptide antigen of polypeptide having the Δ5 fatty acid desaturation activity can be produced in a two-step procedure using anti-idiotypic antibodies. Such a method uses the fact that antibodies are themselves antigens, and thus it is possible to obtain the antibody binding to a second antibody. According to this method, the antibody specifically binding to the polypeptide having the Δ5 fatty acid desaturation activity is used to immunize an animal (preferably a mouse). Then, the splenocytes from such animal are used to produce hybridoma cells, and the hybridoma cells are screened to identify clones which produce the antibody wherein the ability to bind to the antibody capable of specifically binding to the polypeptide having the Δ5 fatty acid desaturation activity can be blocked by an antigen of the polypeptide having the Δ5 fatty acid desaturation activity. The antibody includes anti-idiotypic antibodies to the antibody capable of specifically binding to the polypeptide having the Δ5 fatty acid desaturation activity and is used to immunize an animal to induce formation of further antibodies capable of specifically binding to the polypeptide having the Δ5 fatty acid desaturation activity.

It is apparent that Fab and F(ab')$_2$ fragments as well as other fragments of the antibodies in accordance with the present invention can be used according to the methods disclosed herein. Such fragments are typically produced by proteolytic cleavage, using enzymes such as papain (to produce Fab fragments) or pepsin (to produce F(ab')$_2$ fragments). Alternatively, fragments binding to the polypeptide having the Δ5 fatty acid desaturation activity can be produced by applying recombinant DNA technology or by synthetic chemistry.

As described above, the antibody in accordance with the present invention is only necessary to have an antibody fragment (e.g., Fab and F(ab')$_2$ fragments) that recognizes at least the polypeptide having the Δ5 fatty acid desaturation activity. It should thus be noted that immunoglobulins comprising the antibody fragment which recognizes the polypeptide having the Δ5 fatty acid desaturation activity and the Fc fragment having a different antibody molecule are also included in the present invention.

That is, an object of the present invention is to provide the antibody which recognizes the polypeptide having the Δ5 fatty acid desaturation activity, but not to provide individual immunoglobulin species (IgA, IgD, IgE, IgG or IgM), methods for producing chimeric antibodies, methods for producing peptide antigens, etc., specifically described herein. It should thus be noted that antibodies which can be obtained by the other methods are also deemed to be within the technical scope of the present invention.

(4) Use of the Polypeptide and/or Polynucleotide in Accordance with the Present Invention (4-1) Vector The present invention provides a vector used to produce the polypeptide having the Δ5 fatty acid desaturation activity. The vector in accordance with the present invention may be the vector used for in vitro translation or a vector used for recombinant expression.

The vector in accordance with the present invention is not particularly limited, so long as the vector comprises the polynucleotide in accordance with the present invention. For example, the vector includes a recombinant expression vector inserted with cDNA of the polynucleotide encoding the polypeptide having the Δ5 fatty acid desaturation activity, and the like. The method of producing the recombinant expression vector includes a method using a plasmid, phage or cosmid, etc., but is not particularly limited thereto.

The vector is not particularly limited to its specific kinds but such a vector that can be expressed in host cells may be appropriately chosen. In more detail, a promoter sequence is appropriately chosen to express the polynucleotide in accordance with the present invention certainly depending upon kind of host cells, this promoter sequence and the polynucleotide in accordance with the present invention are incorporated into various plasmids, etc., and the vectors thus obtained may be used as expression vectors.

The expression vectors preferably includes at least one selection marker. Such markers include dihydrofolate reductase or neomycin resistance for the incubation eukaryotic cells and tetracycline- or ampicillin-resistant genes for the incubation in *E. coli* and other bacteria.

By using the selection markers described above, it can be confirmed whether or not the polynucleotide in accordance with the present invention is introduced into host cells and further whether the polynucleotide is certainly expressed in host cells or not. Also, the polypeptide in accordance with the present invention may be expressed as a fused polypeptide; for example, green fluorescent polypeptide GFP (Green Fluorescent Protein) derived from jelly fish or *Aequorea victoria* may be used as the marker to express the polypeptide in accordance with the present invention as a GFP-fused polypeptide.

Various cells heretofore known can be advantageously used as the host cells described above, without any particular restriction. Specific examples include, but are not limited to, bacterial such as *Escherichia coli*, etc., yeasts (*Saccharomyces cerevisiae, Schizosaccharomyces pombe*), oocytes of *Caenorhabditis elegans* or *Xenopus laevis*, etc. Culture media and conditions suitable for the host cells described above are well known in the art.

Methods for introducing the vector, namely, transformation methods are not particularly limited and methods known in the art can be advantageously used; the methods include the electroporation, calcium phosphate, liposome and DEAE-dextran methods, etc. Also where the polypeptide in accordance with the present invention is transgenically expressed in insects, the expression system using baculovirus may be employed.

As described above, it is sufficient for the vector in accordance with the present invention so long as the vector comprises at least the polynucleotide encoding the polypeptide in accordance with the present invention. It should thus be noted that vectors other than the expression vectors are also deemed to be within the technical scope of the present invention.

In summary, an object of the present invention is to provide the vector comprising the polynucleotide encoding the polypeptide in accordance with the present invention, but not to provide each vector and cell species specifically described herein as well as methods of producing these vectors or introducing these cells. It should thus be noted that vectors obtained by other methods of producing vectors using vector species other than those described above are also deemed to be within the technical scope of the present invention.

(4-2) Transformant or Cell

The present invention provides the transformant or cell in which the polynucleotide encoding the polypeptide having the Δ5 fatty acid desaturation activity described above is introduced. Herein, the "transformant" is used to mean not only a tissue or organ but also an individual organism.

Methods of preparing (producing) the transformant or cell are not particularly limited, and include, for example, the aforesaid method which involves transformation through incorporation of a recombinant vector into a host. Organisms to be transformed are not particularly limited, and include various microorganisms, plants or animals illustratively shown for the host cells described above.

The transformant or cell in accordance with the present invention is characterized in that its compositions are altered from those of naturally occurring fatty acids. The transformant or cell in accordance with the present invention is preferably a plant or its progeny, or tissues derived therefrom, more preferably, rice plant or tobacco.

The plant transformant comprising the polynucleotide encoding the polypeptide in accordance with the present invention can be obtained by introducing the recombinant vector comprising the polynucleotide into a plant to be capable of expressing the gene.

Where the recombinant expression vector is used, the recombinant expression vector used to transform the plant is not particularly limited so long as the vector is capable of expressing the polynucleotide in accordance with the present invention in the plant. Examples of such vectors include a vector bearing a promoter capable of constitutively expressing the polynucleotide in plant cells (e.g., a cauliflower mosaic virus 35S promoter) in plant cells, and a vector inducibly activated through external stimulation.

Plants which are to be the target of transformation in the present invention may be any of entire plant bodies, plant organs (e.g., leaves, petals, stems, roots, seeds, etc.), plant tissues (e.g., epidermis, phloem, parenchyma, xylem, vascular bundles, palisade tissues, spongy tissues, etc.) or plant culture cells or various types of plant cells (e.g., suspension culture cells), protoplasts, leaf slices, callus, and the like. Specific examples of plant species which may be used for transformation include, but are not limited to, those belonging to the Monocotyledoneae or the Dicotyledoneae.

For gene transformation into plants, conventional transformation methods known to one skilled in the art (e.g., the Agrobacterium method, gene gun, the PEG method, the electroporation method, etc.) are used. For example, the Agrobacterium-mediated method and the method of directly introducing into plant cells are well known. When the Agrobacterium method is used, a plant expression vector constructed is transferred into an appropriate Agrobacterium strain (e.g., Agrobacterium tumefaciens), followed by infection of aseptically cultured leaf discs with this strain, according to the leaf disc method (Hirobumi Uchimiya, Manuals for Plant Gene Manipulation, 1990, pp. 27-31, Kodansha Scientific Co., Ltd., Tokyo). Thus, the transgenic plant can be obtained. In addition, the method of Nagel, et al. (Micribiol. Lett., 67, 325 (1990)) may be used. This method involves introducing first, e.g., an expression vector into Agrobacterium and then introducing the transformed Agrobacterium into plant cells or plant tissues according to the method described in Plant Molecular Biology Manual (S. B. Gelvin et al., Academic Press Publishers). Herein, the "plant tissue" includes callus, which is obtained by culturing plant cells. When the transformation is carried out using the Agrobacterium method, binary vectors (pBI121 or pPZP202, etc.) can be used.

For direct transfer of the gene into plant cells or plant tissues, the electroporation method and the gene gun method are known. When the gene gun is used, entire plant bodies, plant organs or plant tissues per se may be used, or may be used after preparation of protoplasts. The samples thus prepared can be bombarded using a gene transfer apparatus (e.g., PDS-1000 (BIO-RAD, Inc.), etc.). Bombardment conditions vary depending upon type of the plant or sample. Usually, the sample is bombarded under a pressure of about 450-2000 psi at a distance of 4-12 cm.

The transgenic cells or plant tissues are first selected by chemical resistance such as hygromycin resistance, etc. and then regenerated into plant bodies in a conventional manner. Regeneration of plant bodies from the transformants can be performed by methods known to one skilled in the art, depending upon kind of plant cells.

When a plant culture cell is used as the host, transformation is effected by introducing the recombinant vector into the plant culture cell by the gene gun method, the electroporation method, etc. Callus, shoots, hairy roots, etc. resulted from the transformation can be used directly in cell culture, tissue culture or organ culture. Furthermore, they can be regenerated into plant bodies by conventional plant tissue culture methods through administration of plant hormones (e.g., auxin, cytokinin, gibberellin, abscisic acid, ethylene, brassinolide, etc.) at appropriate concentrations.

PCR, Southern hybridization, northern hybridization or the like, can be used to confirm whether the gene has been introduced into the host or not. For example, DNA is prepared from the transgenic plant and then DNA-specific primers are designed for PCR. The PCR reaction can be performed under the same conditions as used for the preparation of plasmids described above. Subsequently, the amplified product is subjected to agarose gel electrophoresis, polyacrylamide gel electrophoresis, capillary electrophoresis, etc. and stained with ethidium bromide, SYBR Green solution, etc. By detecting the amplified product as a single band, the transformation can be confirmed. Alternatively, PCR may be performed using primers previously labeled with a fluorescent dye, etc. and then, the amplified product can be detected. Furthermore, there may be employed a method which involves binding the amplified product to a solid phase such as a microplate, etc. and then confirming the product by fluorescence or enzyme reactions.

Once the transgenic plant wherein the polynucleotide in accordance with the present invention is integrated in the genome is acquired, its progeny can be obtained by sexual or asexual reproduction of the plant body. Also, the plant body can be mass-produced by acquiring from the plant body or its progeny or clones thereof, e.g., seeds, fruits, cut panicles, tubers, tuberous roots, strains, callus, protoplasts, etc., and then using them as the origin. Accordingly, the present invention also includes the plant body in which the polynucleotide in accordance with the present invention is expressly introduced, or progenies of the plant body having the same property as in the plant body, and tissues derived therefrom.

The plant used is not particularly limited and preferably used is, for example, a tobacco plant. Like petunia the tobacco plant is a typical plant which is susceptible to transformation and capable of regenerating from a cell wall-removed single cell (protoplast) to a single plant body. This single plant body regenerated does not result in a chimeric pattern unlike a single body derived from multiple cells so that its transformants can be efficiently produced.

A preferred example of the transformation method for tobacco is the leaf disc method. According to this method, operations are easy and multiple independent transformants can be obtained from a single leaf disc. The transformation method is described in, e.g., "Shin-Seibutsu Kagaku Jikken-no-Tebiki (New Guidance of Biochemical Experiment) 3: Isolation/Analysis of Nucleic Acid and Gene Research Method, published by Kagaku Dojin, 1996.

Specifically, a leaf disc is excised from an aseptically grown tobacco leaf on a sterile Petri dish and the excised leaf disc is pre-incubated in NB medium. Next, the pre-incubated leaf disc is impregnated with an *Agrobacterium*-infected bacteria solution for co-incubation. The leaf disc is embedded in NB medium supplemented with carbenicillin and kanamycin. After subculture is made until shoots generate via callus formation from the leaf disc, the shoots are obtained. At the point of time when the shoots grow and distinction becomes clear between the stems and leaves, the shoots are excised from the stems and transferred to MS medium free of either any antibiotic or any hormone. After the excised shoots produce roots, the roots are grown in a greenhouse. The shoots are transferred to a hormone-supplemented medium to promote rooting. At the same time, the leaves are partially excised from the shoots and transplanted to an assay medium supplemented with carbenicillin and kanamycin. Approximately 10 days after the transplantation, the leaves which induce callus are regarded as kanamycin-resistant individuals and thus recovered, whereas the leaves which turn brown are regarded as kanamycin-sensitive individuals and thus discarded.

By using the transgenic plant thus obtained, pinolenic acid or coniferonic acid is produced in the plant body so that pinolenic acid or coniferonic acid can be produced by a low cost and environmentally-friendly production process.

Generally, when a gene originating from a heterologous organism is expressed in a plant, it is difficult to predict how well the gene will function in the plant, since there are steps of transcription, translation, subsequent modification, etc. However, it is sufficient in higher plants to introduce only one $\Delta 6$ desaturase-encoding gene in order to synthesize $\gamma$-linolenic acid from linoleic acid as an ordinary fatty acid, and many successful examples are reported in creating higher plants, to which the $\gamma$-linolenic acid synthesis ability is imparted. For instance, the $\Delta 6$ desaturase gene from borage is expressed in tobacco plants (Proc. Natl. Acad. Sci. USA 94, 4211, 1997), the $\Delta 6$ desaturase gene from ethium is expressed in tobacco plants (Lipids, 37, 412, 2002), the $\Delta 6$ desaturase gene from the fungus Pythium irregulare is expressed in tobacco plants (Plant Physiol. 129, 354, 2002), etc. Since pinolenic acid is also synthesized from linoleic acid by only one $\Delta 5$ desaturase, it is readily understood to one skilled in the art that by introducing the recombinant expression vector comprising the polynucleotide encoding the polypeptide having the $\Delta 5$ fatty acid desaturation activity, the pinolenic acid synthesis ability can be imparted to higher plants, following the description herein.

The transformation methods for many plants are already reported. Examples of transformable plants include soybean, rapeseed, sesame, palm, cotton, rice plant, barley, wheat, potato, tomato, poplar, banana, eucalyptus, sweet potato, alfalfa, lupine, linum, common bean, lettuce, radish, corn, cauliflower, rose, chrysanthemum, carnation, snapdragon, cyclamen, orchid, Prairie gentian, freesia, gerbera, gladiolus, gypsophila, kalancoe, lily, pelargonium, geranium, petunia, torenia, tulip, etc.

One embodiment for producing rice transformants is described below.

The polynucleotide in accordance with the present invention is introduced into the binary vector pPZP202 harboring a hygromycin-resistant gene to construct the transformant vector. The polynucleotide in accordance with the present invention is operably linked to promoter CaMV35S in-frame.

Using the transformant vector obtained, *Agrobacterium tumefaciens* EHA101 is transformed by electroporation under selection on 50 mg/l kanamycin and hygromycin. The resulting *Agrobacterium* transformant is stored frozen until use.

Brown rice grains are prepared by removing the lemmas from wild-type seeds followed by sterilization with 70% ethanol for 3 minutes and then washing 3 times with sterilized distilled water. The grains are further sterilized with 50% sodium hypochlorite for 30 minutes and then washed 5 times with sterile distilled water. The brown rice grains are placed on the callus induction medium containing N6 medium (Chu et al., 1975, Sci. Sinica, 18, 659-668) supplemented with 30 g/l sucrose, 0.3 g/l casamino acid, 2.8 g/l proline and 2.0 mg/l 2,4-D, which is solidified with 4.0 g/l Gelrite. Prior to autoclaving, pH of the medium is adjusted to 5.8. The brown rice grains are grown at 28° C. for 4 weeks in bright light to produce calli in a size of about 5 mm. The calli are used for *Agrobacterium* infection.

The *Agrobacterium* stored frozen in glycerol is cultured on AB medium (Chilton et al., 1974, Proc. Natl. Acad. Sci. USA, 71, 3672-3676) supplemented with 20 mg/l kanamycin, 50 mg/l hygromycin and 100 mg/l spectinomycin, which is adjusted to pH 7.2 and solidified with 15 g/l agar, at 28° C. for 3 days in the dark. The *Agrobacterium* bacteria are collected and suspended in liquid AAM medium (Hiei et al., 1994) supplemented with 10 mg/l acetosyringone (Hiei et al., 1994, Plant J., 6, 271-282). The calli described above are immersed in the resulting suspension for 2 minutes and blotted on a sterile paper towel to remove excess moisture, the calli are transferred to the 10 mg/l acetosyringone-containing callus induction medium described above. Co-cultivation is performed at 28° C. for 3 days for *Agrobacterium* infection. The resulting infected calli are washed 10 times with sterilized distilled water and finally once with sterilized distilled water containing 500 mg/l carbenicillin to remove excess moisture with a sterile paper towel. These calli are cultivated at 28° C. for 2 weeks in the callus induction medium described above supplemented with 10 mg/l acetosyringone, 50 mg/l hygromycin and 300 mg/l carbenicillin, followed by further cultivation for 4 weeks in the callus induction medium supplemented with 50 mg/l hygromycin and 100 mg/l carbenicillin. Hygromycin-resistant calli are selected and transferred to regeneration medium containing MS basal medium (Murashige and Skoog, 1962, Physiol. Plant., 15, 473-497), pH 5.8, supplemented with 30 g/l sucrose, 30 g/l sorbitol, 2 g/l casamino acid, 2.2 mg/l kinetin, 1.0 mg/l NAA, 100 mg/l carbenicillin, 50 mg/l hygromycin and 4 g/l Gelrite.

The transformant thus obtained can be readily regenerated in a hygromycin-containing regeneration medium and transferred to soil for cultivation.

As described above, it is sufficient for the transformant or cell in accordance with the present invention that at least the polynucleotide encoding the polypeptide in accordance with the present invention is introduced therein. It should thus be noted that transformants or cells produced by means other than those using the recombinant expression vector are also deemed to be within the technical scope of the present invention.

As described above, the polypeptide in accordance with the present invention has the activity of Δ5 desaturating linoleic acid; in addition, the polypeptide further has the activity of Δ5 desaturating α-linolenic acid and the activity of Δ7 desaturating dienoic acids or trienoic acids having 20 carbon atoms. Therefore, use of the transformants or cells in accordance with the present invention should not be limited only to the Δ5 desaturation of linoleic acid to produce pinolenic acid.

In other words, an object of the present invention is to provide the transformants or cells characterized in the polynucleotide encoding the polypeptide in accordance with the present invention is introduced therein, but not to provide individual vector species and methods for introduction specifically described herein. It should thus be noted that transformants and cells using vector and cell species as well as methods of producing vectors and methods of introducing cells other than those described above are also deemed to be within the technical scope of the invention.

(4-3) Method of Producing Polypeptide

The present invention provides the method of producing the polypeptide in accordance with the present invention.

In one embodiment, the method of producing the polypeptide in accordance with the present invention is characterized by using the vector comprising the polynucleotide encoding the polypeptide in accordance with the present invention.

In one aspect of this embodiment, the vector described above is preferably used for the cell-free protein synthesis system in the method of producing the polypeptide in accordance with this embodiment. Where the cell-free protein synthesis system is used, a variety of commercially available kits may be used. Preferably, the method of producing the polypeptide in accordance with this embodiment includes the step of incubating the vector described above and the solution for the cell-free protein synthesis.

In another aspect of this embodiment, it is preferred to use the recombinant expression system in the method of producing the polypeptide in accordance with this embodiment. Where the recombinant expression system is used, there may be adopted a method in which the polynucleotide in accordance with the present invention is incorporated into a recombinant expression vector, the vector is then expressibly introduced into a host by a publicly known method, and the polypeptide described above is purified; and so on. The recombinant expression vector may be or may not be a plasmid, as far as the objective polynucleotide can be introduced into a host. Preferably, the method of producing the polypeptide in accordance with this embodiment includes the step of introducing the vector described above into a host.

Where an exogenous polynucleotide is introduced into a host as such, it is preferred that a promoter having the function in the host to express the exogenous polynucleotide is incorporated in the expression vector. Though methods for purification of the polypeptide recombinantly produced are different depending upon host used and properties of the polypeptide, the objective polypeptide can be purified relatively easily by using a tag, etc.

Preferably the method of producing the polypeptide in accordance with this embodiment further includes the step of purifying the aforesaid polypeptide from the extract of cells or tissues containing the polypeptide in accordance with the present invention. The step of purifying the polypeptide preferably comprises preparing the cell extract from cells or tissues by well-known methods (e.g., a method which comprises destroying cells or tissues, centrifuging and recovering soluble fractions), followed by purifying the polypeptide from the cell extract by well-known methods (e.g., ammonium sulfate or ethanol precipitation, acid extraction, anion or cation exchange chromatography, phosphocellulose chromatography, hydrophobic interaction chromatography, affinity chromatography, hydroxyapatite chromatography and lectin chromatography), but is not limited thereto. Most preferably, high performance liquid chromatography (HPLC) is employed for purification.

In yet another embodiment, the method of producing the polypeptide in accordance with the present invention is characterized by purifying the said polypeptide from cells or tissues capable of naturally expressing the polypeptide in accordance with present invention. Preferably, the method of producing the polypeptide in accordance with this embodiment includes the step of identifying the cells or tissues capable of naturally expressing the polypeptide in accordance with the present invention using the antibody or oligonucleotide described above. More preferably, the method of producing the polypeptide in accordance with this embodiment further includes the aforesaid step of purifying the polypeptide.

In yet further embodiment, the method of producing the polypeptide in accordance with the present invention is characterized by chemically synthesizing the polypeptide in accordance with the present invention. One skilled in the art will readily understand that the polypeptide in accordance with the present invention as described herein can be chemically synthesized by applying well-known chemical synthesis technology, based on the amino acid sequence of the polypeptide in accordance with the present invention.

As described above, the polypeptide acquired by the method of producing the polypeptide in accordance with the present invention may be variant polypeptides present naturally or variant polypeptides produced artificially.

Methods of producing the variant polypeptides are not particularly limited. The variant polypeptides can be produced by well known methods of producing variant polypeptides, for example, site-specific mutagenesis (see, e.g., Hashimoto-Gotoh, Gene 152, 271-275 (1995)), a method of producing variant polypeptides, which involves introducing point mutations into base sequences using PCR, a method of producing mutants by transposon insertion, etc. The variant polypeptides can also be produced using commercially available kits.

As described above, the polypeptide in accordance with the present invention can be produced by known conventional techniques, at least based on the amino acid sequence of the polypeptide having the Δ5 fatty acid desaturation activity, or the base sequence of the polynucleotide encoding the polypeptide having the Δ5 fatty acid desaturation activity.

In other words, an object of the present invention is to provide the method of producing the polypeptide having the Δ5 fatty acid desaturation activity. It should be noted that the method further including steps other than the various steps described above is also deemed to be within the technical scope of the present invention.

(4-4) Method of Producing Fatty Acid

The present invention provides the method of producing fatty acids using organisms or cells capable of expressing the polypeptide in accordance with the present invention. The organisms described above may be naturally occurring intact organisms or transformants acquired using the recombinant expression system.

In one embodiment, the method of producing fatty acids in accordance with the present invention is characterized by producing fatty acids using the organism transformed with the polynucleotide encoding the polypeptide in accordance with the present invention or its tissues. Preferably, the organism described above is yeast or plant.

In a preferred aspect of this embodiment, the method of producing fatty acids in accordance with the present invention involves the step of introducing the polynucleotide encoding the polypeptide in accordance with the present invention into yeast or plant. For the step of introducing the polynucleotide into yeast or plant, those various gene transfer methods described above may be used. In this aspect of this embodiment, the yeast or plant has different compositions between fatty acids produced before transformation and those produced after transformation. Specifically, the fatty acids obtained from the yeast or plant described above provides an increased content of pinolenic acid and/or coniferonic acid. The method of producing fatty acids in accordance with this aspect of this embodiment preferably further includes the step of extracting the fatty acids from the yeast or plant described above.

Plant oil containing the fatty acids extracted from the transgenic plant in accordance with the present invention, in which the content of, e.g., pinolenic acid increases as described above, is provided as a pinolenic acid-rich food. In addition, not only the fatty acids extracted but seeds, fruits, cut panicles, tubers and/or tuberous roots, etc. of the transgenic plant described above can be provided as pinolenic acid-rich foods. The target for modification of the fatty acid composition is not particularly limited and in addition to plants, all organisms including animals, bacteria, yeasts, etc. can be the targets to be modified.

In another embodiment, the method of producing fatty acids in accordance with the present invention involves the step of introducing the oligonucleotide in accordance with the present invention as an antisense oligonucleotide into the yeast or plant capable of naturally expressing the polypeptide in accordance with the present invention. In the step of introducing the oligonucleotide into yeast or plant, the antisense RNA technique described above may be employed. The method of producing fatty acids in accordance with this embodiment preferably further includes the step of identifying the yeast or plant capable of naturally expressing the polypeptide in accordance with the present invention using the antibody or oligonucleotide described above. The method of producing fatty acids in accordance with this embodiment preferably further includes the step of extracting the fatty acids from the yeast or plant described above.

In this embodiment, the yeast or plant has different compositions between fatty acids produced before introduction of the oligonucleotide described above and those produced after the introduction. Specifically, the fatty acids obtained from the yeast or plant described above provides a decreased content of naturally occurring pinolenic acid and/or coniferonic acid.

As described above, it may be sufficient to use organisms capable of expressing at least the polypeptide in accordance with the present invention in the method of producing fatty acids in accordance with the present invention.

In other words, an object of the present invention is to provide the method of producing fatty acids, using the organism having a fatty acid composition modified by the polypeptide in accordance with the present invention. It should be noted that production methods using animals, plants or various cells as the organisms described above are also deemed to be within the technical scope of the present invention.

(4-5) Food and Industrial Product

The present invention provides foods and industrial products manufactured using the fatty acids, which are obtained by the method of producing fatty acids described above. The foods referred to in this section may be any of seeds, fruits, cut panicles, tubers and/or tuberous roots, etc. of the transgenic plant described above, or may be foods (e.g., plant oils for cooking) manufactured using the fatty acids extracted from the transgenic plant described above.

Pinolenic acid has multiple double bonds in its molecule and based on this unique physical property, can be used as a raw material for industrial products (industrial products, e.g., films, biodegradable plastics, functional fibers, lubricant oils or detergents). Pinolenic acid was produced so far by extraction from pine seeds, which encounters problems that pinolenic acid cannot be produced in a large scale, resulting in high production costs and pines as the supply source of pinolenic acid are limited in forest resources, and so on. According to the present invention, pinolenic acid can be mass-produced at low costs.

(4-6) Detector

The present invention provides a variety of detectors. The detector in accordance with the present invention comprises a substrate having immobilized thereon the polynucleotide in accordance with the present invention or its fragment, or a substrate having immobilized thereon the polypeptide or antibody in accordance with the present invention. The detector can be used for detection/determination of expression patterns of the polynucleotide and polypeptide in accordance with the present invention, etc., under various conditions.

In one embodiment, the detector in accordance with the present invention is characterized by immobilizing the polynucleotide and/or oligonucleotide in accordance with the present invention on a substrate. In a preferred aspect of this embodiment, the detector in accordance with the present invention is a so-called DNA chip. As used herein, the term "DNA chip" means, but is not limited to, a synthetic type DNA chip wherein a synthesized oligonucleotide is immobilized on a substrate and further includes a slide glass type DNA microarray wherein cDNA from PCR products, etc. is immobilized on a substrate. The DNA chip includes, for example, a DNA chip wherein a probe capable of specifically hybridizing the gene of the present invention (i.e., the oligonucleotide in accordance with the present invention) is immobilized on a substrate (carrier).

Sequences used as the probe can be determined by known methods of identifying characteristic sequences from the cDNA sequences (examples include, but are not limited to, the SAGE method (Serial Analysis of Gene Expression) (Science 276:1268, 1997; Cell 88:243, 1997; Science 270:484, 1995; Nature 389:300, 1997; U.S. Pat. No. 5,695,937), etc.)

In fabrication of the DNA chip, publicly known methods may be used. For example, where a synthetic oligonucleotide is used as the oligonucleotide, the oligonucleotide may be synthesized on a substrate by photolithography technique in combination with solid phase DNA synthesis technique. On the other hand, when cDNA is used as the oligonucleotide, cDNA may be applied onto a substrate using an array machine.

Like ordinary DNA chips, a perfect match probe (oligonucleotide) and a mismatch probe with a single base substitution in the perfect match probe may be disposed to achieve a higher degree of the detection accuracy of the polynucleotide. Further for detecting different polynucleotides in parallel, multiple oligonucleotides may be immobilized on the same substrate to fabricate the DNA chip.

A material for the substrate used in the detector in accordance with this embodiment may be any material, as long as it can stably immobilize the polynucleotide or oligonucleotide thereon. In addition to the substrate described above, examples include, but are not limited to, synthetic resins such as polycarbonates, plastics, etc., glass, etc. Shape of the substrate is not particularly limited, and a plate-like or film-like substrate, etc. can be advantageously used. In a preferred aspect of this embodiment, the detector in accordance with this embodiment are used for the detection of cDNA libraries prepared from various organisms or their tissues or cells as the target sample.

In another embodiment, the detector in accordance with the present invention is characterized in that the polypeptide or antibody in accordance with the present invention is immobilized on a substrate. In a preferred aspect of this embodiment, the detector in accordance with this embodiment is a so-called protein chip.

As used herein, the term "substrate" is intended to mean any substance on which the objective product (e.g., the polynucleotide, oligonucleotide, polypeptide or protein) can be carried, and used interchangeably with the term "support." Examples of preferred substrate (support) include, but are not limited to, beads (e.g., polystyrene beads), solid phases (e.g., glass tubes, reagent strips, polystyrene-made microtiter plates or amino group bonding type microtiter plates), etc. Procedures to immobilize the objective product on these substrates are well known to one skilled in the art and described in, for example, Nature 357: 519-520 (1992) (which is hereby incorporated by reference).

A material for the substrate used in the detector in accordance with this embodiment may be any material, so long as it can stably immobilize the polypeptide or antibody thereon. In addition to the substrates described above, examples include, but are not limited to, synthetic resins such as polycarbonates, plastics, etc., glass, etc. Shape of the substrate is likewise not particularly limited, and a plate-like or film-like substrate, etc. can be advantageously used.

Methods other than the methods described above for immobilization of the polypeptide or antibody on a substrate include, for example, a physical adsorption method which involves spotting, like dot blotting, the polypeptide or antibody onto a nitrocellulose membrane or a PDVF membrane, or a method which involves bonding a polyacrylamide pad on a slide glass and spotting the polypeptide or antibody thereon to reduce denaturation of the polypeptide or antibody. Also, there may be used a method which involves using an aldehyde-modified glass, not only to adsorb the polypeptide or antibody onto a substrate surface but also to bind them firmly (G. MacBeath, S. L. Schreiber, Science, 289, 1760 (2000)). Besides, for immobilizing the polypeptide on a substrate in a uniform orientation, there may be used a method for immobilization on a nickel complex-coated surface of the substrate via its oligohistidine tag (H. Zhu, M. Bilgin, R. Bangham, D. Hall, A. Casamayor, P. Bertone, N. Lan, R. Jansen, S. Bidlingmaier, T. Houfek, T. Mitchell, P. Miller, R. A. Dean, M. Gerstein, M. Snyder, Science, 293, 2101 (2001)).

In a preferred aspect of this embodiment, the detector in accordance with this embodiment can be used for detection using as the target sample the extract from various organisms or their tissues or cells.

As described above, it is sufficient for the detector in accordance with the present invention to comprise a support having immobilized thereon, at least, the polynucleotide or oligonucleotide in accordance with the present invention, or, the polypeptide in accordance with the present invention or the antibody capable of binding to said polypeptide. In other words, it is sufficient for the detector in accordance with the present invention to have a substrate having immobilized thereon the polynucleotide or oligonucleotide in accordance with the present invention, or, the polypeptide in accordance with the present invention or the antibody capable of binding to the polypeptide. It should thus be noted that detectors having elements other than these supports (including substrates) are also deemed to be within the technical scope of the present invention.

That is to say, an object of the present invention is to provide an instrument for detecting the polypeptide in accordance with the present invention, the polynucleotide in accordance with the present invention or the polypeptide capable of binding to the antibody in accordance with the present invention, but not to provide individual supports or methods for immobilization specifically described herein. It should thus be noted that detectors having other elements than the supports described above are also deemed to be within the technical scope of the present invention.

The present invention will be described in more detail with reference to EXAMPLES below but is not deemed to be limited thereto.

EXAMPLES

The procedures used in these EXAMPLES were carried out, following those described in Molecular Cloning (Sambrook et al., Cold Spring Harbour Laboratory Press, 1989), unless otherwise indicated.

Example 1

Fatty Acid Composition of *Chlamydomonas* (*C. reinhardtii*)

FIG. 1 shows the results of GC analysis of fatty acid methyl esters for *C. reinhardtii*. The fatty acids were identified by comparing with the retention times of the standard methyl esters and the mass spectra of pyrrolidine derivatives of these standard fatty acids. According to the results of GC-MS analysis, *C. reinhardtii* shows 16:0, 16:1Δ7, 16:3Δ7,10,13, 16:4Δ4,7,10,13, 18:0, 18:1Δ9, 18:1Δ11, indicating that it contains, in addition to linoleic acid (LA, 18:2Δ9,12) and α-linolenic acid (ALA, 18:3Δ9,12,15), pinolenic acid (PA, 18:3Δ5,9,12) and coniferonic acid (CA, 18:4Δ5,9,12,15). Δ6 desaturated C18 fatty acids such as γ-linolenic acid (GLA, 18:3Δ6,9,12) and stearidonic acid (STA, 18:4Δ6,9,12,15) or unsaturated C18 or higher fatty acids were not detected (see FIG. 1 and TABLE 1). Each data in TABLE 1 is a mean±standard deviation in 3 independent runs. The contents of PA and CA based on the total fatty acids were 7.7% and 1.7%, respectively. The present invention made it clear for the first time that *C. reinhardtii* contains pinolenic acid.

TABLE 1

| Fatty acid | wt % |
| --- | --- |
| 16:0 | 31.6 ± 1.0 |
| 16:1$^{\Delta 7}$ | 5.5 ± 0.2 |
| 16:3$^{\Delta 7,10,13}$ | 0.7 ± 0.0 |
| 16:4$^{\Delta 4,7,10,13}$ | 9.3 ± 0.8 |
| 18:0 | 3.8 ± 0.1 |
| 18:1$^{\Delta 9}$ | 6.5 ± 0.3 |
| 18:1$^{\Delta 11}$ | 5.3 ± 0.2 |
| LA; 18:2$^{\Delta 9,12}$ | 8.8 ± 0.0 |
| PA; 18:3$^{\Delta 5,9,12}$ | 7.7 ± 0.0 |
| ALA; 18:3$^{\Delta 9,12,15}$ | 19.1 ± 0.9 |
| CA; 18:4$^{\Delta 5,9,12,15}$ | 1.7 ± 0.1 |

Example 2

Isolation of *Chlamydomonas* Fatty Acid Desaturase Polynucleotide CrDES5

Figure 2:
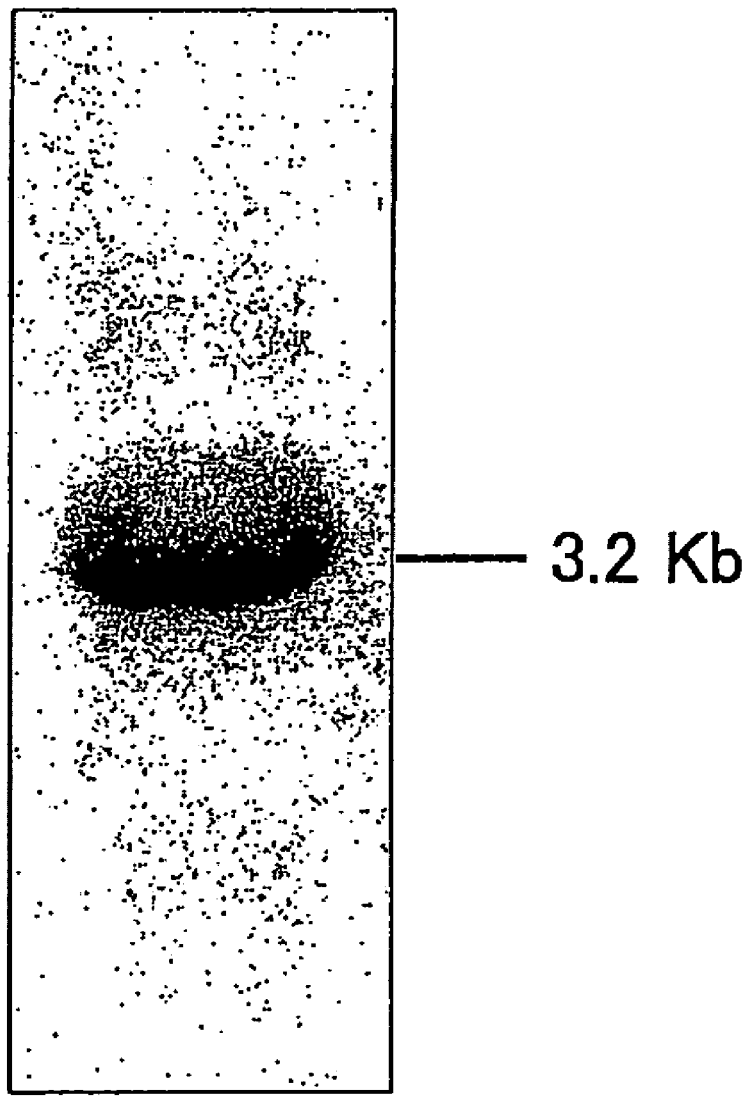
FIG. 2 shows the results of northern analysis of CrDES5.

A cDNA clone assumed to encode the fatty acid desaturase was found by searching an EST database. The cDNA clone LCL007g01 had an insert sequence of 3.2 kb and contained an ORF of 1431 bp encoding 476 amino acid residues. This cDNA was named CrDES5. FIG. 2 shows the results of northern analysis of CrDES5. The total RNA was extracted from the cells of *C. reinhardtii* and hybridized to 32P-labeled DNA fragment from the ORF of CrDES5. The size of the detected transcripts is shown at the right of the lane. The length of the cloned fragment coincided with the results of northern analysis (see FIG. 2).

FIG. 3 shows the alignment in comparison of the amino acid sequence of the *C. reinhardtii* Δ5 desaturase (CrDES5) with the amino acid sequences of Δ5 desaturases for *M. alpina* (MaDES5), *M. polymorpha* (MpDES5) and diatom *P. tricornutum* (PtDES5). The cytochrome b5 domain is marked with dashed line and asterisks are placed on the 8 amino acid residues highly conserved in the cytochrome b5 superfamily. A box border was applied to enclose 3 histidine boxes. A triangle was marked on the glutamine residue conserved in the third histidine box. The residue shown by dot in the table denotes the same residue as the sequence of CrDES5 and the dash denotes alignment gaps. GenBank Accession Nos. of these sequences are AF054824 (MaDES5), AY583465 (MpDES5) and AY082392 (PtDES5). The amino acid sequence of the polypeptide encoded by the ORF of CrDES5 was compared to known desaturases. The CrDES5 polypeptide showed the highest homology (21%) to the Δ5 desaturase of *M. alpine* (see FIG. 3). Like other front-end type desaturases, the N-terminal cytochrome b5 domain functioning as an electron donor and three histidine boxes were conserved also in the CrDES5 polypeptide. Further in the cytochrome b5 domain of CrDES5 polypeptide, the eight amino acid residues marked with asterisks in FIG. 3 coincided with the amino acids conserved throughout the cytochrome b5 superfamily (see Domergue et al., Eur. J. Biochem., p 4105, 2002). Also, the CrDES5 polypeptide has the glutamine residue highly conserved in the third histidine box, like other front-end type desaturases (shown by the inverted triangle in FIG. 3). The foregoing results suggest that the CrDES5 polypeptide is a front-end type desaturase acting on the PUFA (polyunsaturated fatty acid) biosynthesis.

Example 3

Analysis of Function of *Chlamydomonas* Fatty Acid Desaturase Polynucleotide CrDES5

Using vector pPICZA (Zeocin-resistant polynucleotide, manufactured by Invitrogen) bearing the ORF of CrDES5 operably linked to the methanol-inducible 5'AOX1 promoter, the CrDES5 polypeptide was expressed in the methylotrophic yeast *P. pastoris*. The enzyme activity of the CrDES5 polypeptide was determined using the fatty acid composition of this cell as an indicator.

First, the ORF of CrDES5 was amplified using the following primers. *P. pastoris* has the ability to synthesize 18:1Δ9, LA, ALA.

(Primers for Amplification of the ORF of CrDES5)

```
CrDES5-01F:
5'-GCCGAATTCAATATGTGCAGGCCTACCG    (SEQ ID NO: 3)

CrDES5-02R:
5'-GCCGAATTCTTACGCCAGCTTGCGCGCC    (SEQ ID NO: 4)
```

These primers have the underlined EcoRI recognition sequence. PCR was carried out in 20 μl of the reaction solution using 0.5 U Pyrobest DNA polymerase (manufactured by TaKaRa Co., Ltd.) in accordance with the procedures recommended by the manufacturer. PCR conditions: after maintaining at 94° C. for 2 minutes, the reaction was repeated 25 cycles, each cycle set to include 94° C. for 1 minute, 57° C. for 1 minute and 72° C. for 1 minute, followed by cooling at 4° C.

The ORF fragment obtained was digested with EcoRI, subjected to gel purification and ligated with the EcoRI site in the expression vector pPICZA of methylotrophic yeast *P. pastoris*. The construct was named pPICZA-CrDES5.

Using Pichia EasyComp kit (manufactured by Invitrogen), the *P. pastoris* strain PPY1 was transformed with this expression construct pPICZA-CrDES5 and the control vector pPICZA. To express the ORF of CrDES5, each transformant was cultured in minimum medium containing 1.0% glycerol as the sole carbon source using EasySelect Pichia Expression Kit manufactured by Invitrogen by its recommended procedures until OD (600 nm) became 0.5. Thereafter, the transformant was cultured to saturation at 30° C. for 3 days in minimum medium containing 0.5% methanol as the sole carbon source. The fatty acid composition of each transformant cell was determined on GC-MS in accordance with the method described in Kajikawa et al., Biosci. Biotechnol. Biochem., 67, p 605 (2003).

Figure 4:
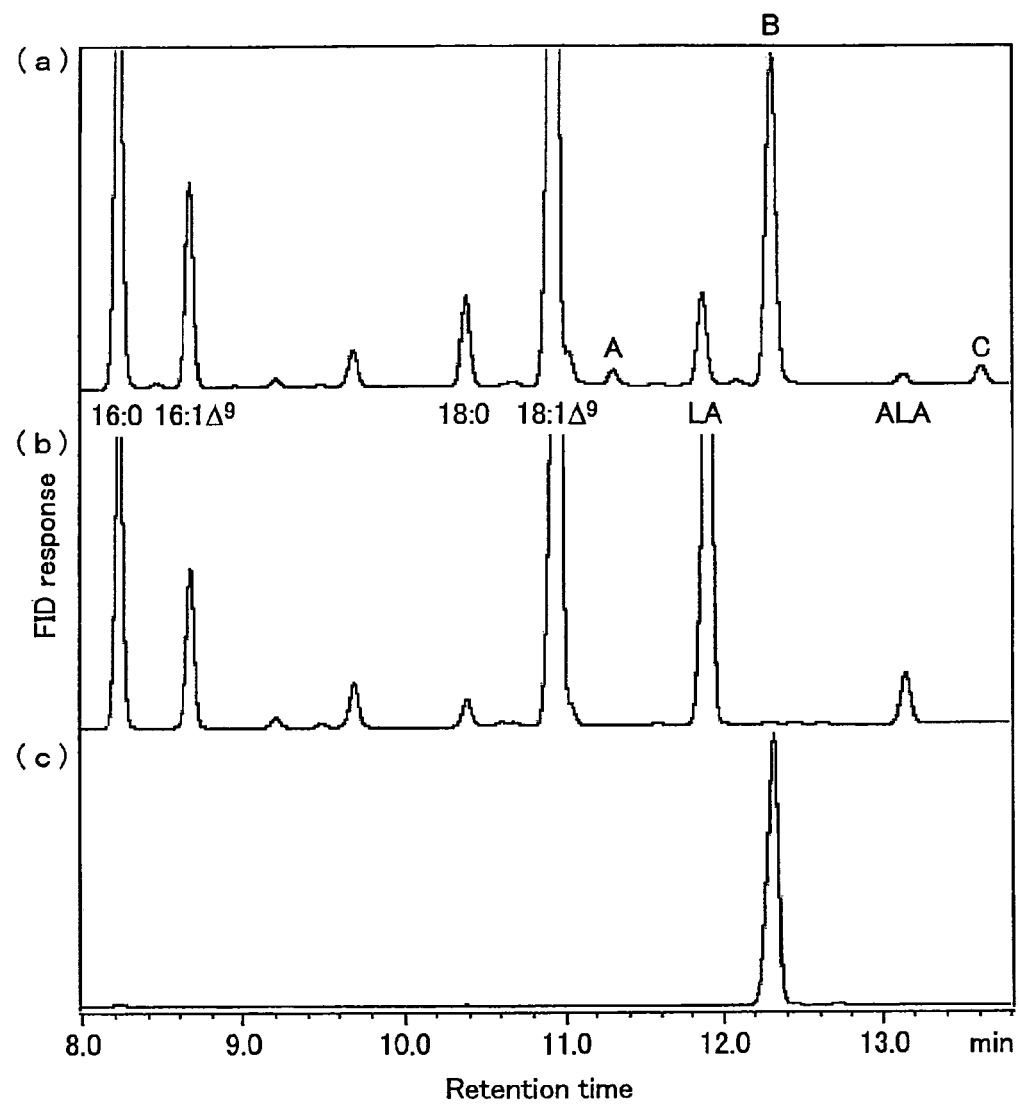
FIG. 4 shows (a) the fatty acid profile of pPICZA-CrDES5-introduced P. pastoris, (b) the fatty acid profile of vehicle vector-introduced P. pastoris and (c) the peak of pinolenic acid standard.

As a result, three new peaks (A, B, C) that were not observed with control were detected in the transformant expressing the ORF of CrDES5 (see TABLE 2 and FIG. 4).

TABLE 2 shows the fatty acid composition of *P. pastoris* transformed with pPICZA-CrDES5 or the control vector pPICZA. In the table, "ND" denotes that data was undetectable. Each value in the table shows a mean±standard deviation in three independent runs.

TABLE 2

| Fatty acid | pPICZA | pPICZA-CrDES5 |
|---|---|---|
| 16:0 | 14.8 ± 0.2 | 18.5 ± 0.5 |
| 16:1$^{\Delta 9}$ | 7.5 ± 0.1 | 8.3 ± 0.2 |
| 18:0 | 1.4 ± 0.3 | 4.6 ± 0.4 |
| 18:1$^{\Delta 9}$ | 43.2 ± 2.0 | 45.3 ± 0.7 |
| 18:1$^{\Delta 5,9}$ | ND | 0.6 ± 0.0 |
| LA; 18:2$^{\Delta 9,12}$ | 30.1 ± 1.9 | 4.4 ± 0.1 |
| PA; 18:3$^{\Delta 5,9,12}$ | ND | 16.7 ± 0.6 |
| ALA; 18:3$^{\Delta 9,12,15}$ | 3.0 ± 0.2 | 0.6 ± 0.2 |
| CA; 18:4$^{\Delta 5,9,12,15}$ | ND | 0.9 ± 0.0 |

FIG. 4 (*a*) shows the fatty acid profile of *P. pastoris* transformed with pPICZA-CrDES5. FIG. 4 (*b*) shows the fatty acid profile of *P. pastoris* transformed with the control vector pPICZA. FIG. 4 (*c*) shows the peak of standard pinolenic acid.

Figure 5:
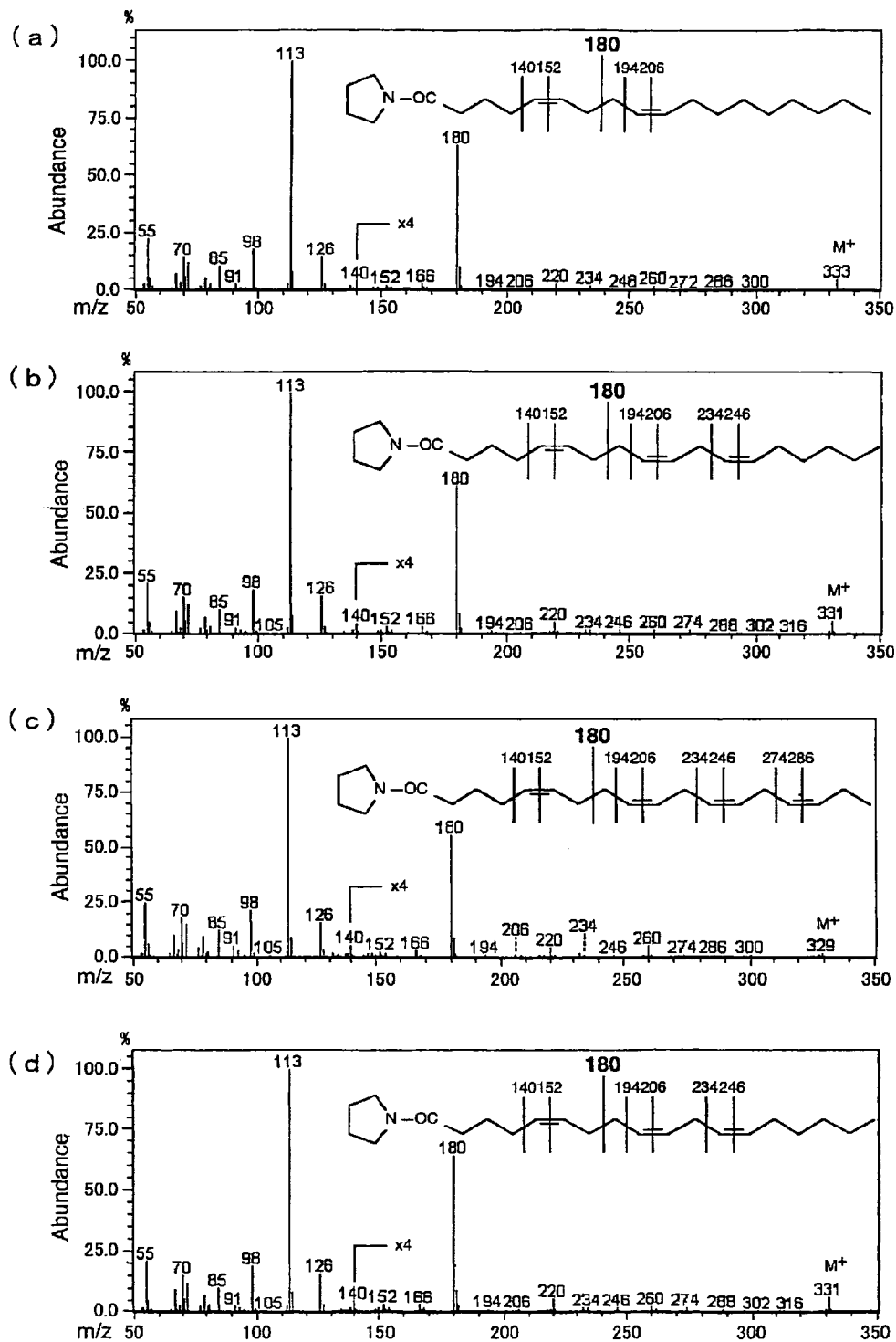
FIG. 5 shows the results of mass spectrometry of pyrrolidine derivatives, which are the reaction products of the CrDES5 desaturase in FIG. 4.

Peak B was detected in the same retention time as in standard pinolenic acid (see FIG. 4). The pyrrolidine derivatives of the fatty acids of *P. pastoris* transformed with pPICZA-CrDES5 or the control vector pPICZA were analyzed on GC-MS (see FIG. 5). Comparison with standard pinolenic acid revealed that new peaks A, B and C were taxolic acid (TA, 18:2Δ5,9), pinolenic acid (PA, 18:3Δ5,9,12) and coniferonic acid (CA, 18:2Δ5,9,12,15).

In the mass spectra for A, the ion peak showing m/z=333 shows the molecular ion peak of TA pyrrolidine derivative. The characteristic fragment ion peak at m/z=180 is thought to originate from cleavage between the carbons at the 7- and 8-positions, due to the presence of two double bonds Δ5 and Δ9. The double bonds Δ5 and Δ9 can be confirmed also from m/z=140 and 152 as well as the fragment ion peaks of 194 and 206 separated by 12 a.m.u. each, respectively.

In the mass spectra for B, the ion peak at m/z=331 shows the molecular ion peak of the PA pyrrolidine derivative, and its fragmentation patterns were identical with the patterns of PA standard. The fragment ion peaks at m/z=140, 152, 180, 194 and 206 indicate the two double bonds of Δ5 and Δ9, as in the case of TA pyrrolidine derivative. In addition, the fragment ion peaks at m/z=234 and 246 indicate the double bond at 12-position.

In the mass spectra for C, the ion peak at m/z=329 indicates the molecular ion peak of CA pyrrolidine derivative. The ion peaks at m/z=140, 152, 180, 194, 206, 234 and 246, which occurred due to fragmentation, indicate the three double bonds of Δ5, Δ9 and Δ12, as in the case of TA and PA pyrrolidine derivatives. In addition, the fragment ion peaks at m/z=274 and 286 indicate the double bond at 15-position.

These results reveal that the CrDES5 polypeptide show the Δ5 desaturation activity for 18:1Δ9, LA, ALA.

Example 4

Substrate Specificity of CrDES5 Polypeptide

The substrate specificity of the CrDES5 polypeptide was examined by adding various fatty acid substrates to the yeast strain transformed with pPICZA-CrDES5 (see TABLE 3). A desaturation efficiency (conversion rate) of the CrDES5 polypeptide to each fatty acid was calculated using the following equation.

Conversion Rate=100×(% of Product)/(% of Substrate+% of Product)

As a result, the highest Δ5 desaturation activity (79.2%) was observed with LA. A relatively high Δ5 desaturation activity (60.0%) was observed with ALA, but only a slight activity (1.0%) was detected in 18:1Δ9. On the other hand, any Δ5 desaturation activity was not detected in the C16 fatty acids, 18:1Δ11, 18:2Δ8E,12, 18:2Δ9,11E, dihomo-γ-linolenic acid (DGLA, 20:3Δ8,11,14) or eicosatetraenoic acid (ETA, 20:4Δ8,11,14,17).

In a similar manner, the activity on dihomolinoleic acid (20:2Δ11,14) and 20:3Δ11,14,17 was measured; dihomopinolenic acid (20:3Δ7,11,14) and 20:4Δ7,11,14,17 were produced, respectively. It has thus been made clear that this gene also encodes the activity of desaturating the Δ7 position of the dienoic and trienoic acids having 20 carbon atoms.

TABLE 3

| substrate | conversion rate (%) |
| --- | --- |
| 16:0 | 0 |
| 16:1$^{Δ9}$ | 0 |
| 16:3$^{Δ7,10,13}$ | 0 |
| 18:0 | 0 |
| 18:1$^{Δ9}$ | 1.3 |
| 18:1$^{Δ11}$ | 0 |
| 18:2$^{Δ8,12}$ | 0 |
| 18:2$^{Δ9,11}$ | 0 |
| LA; 18:2$^{Δ9,12}$ | 79.2 |
| ALA; 18:3$^{Δ9,12,15}$ | 60.0 |
| 20:1$^{Δ11}$ | 0 |
| DGLA; 20:3$^{Δ8,11,14}$ | 0 |
| ETA; 20:4$^{Δ8,11,14,17}$ | 0 |

Example 5

Construction of Vector for Introducing CrDES5 Polynucleotide into Tobacco

In order to express the CrDES5 polynucleotide in tobacco, the expression construct was prepared by the following procedure. First, a DNA fragment bearing the ORF of CrDES5 was excised with XbaI from the construct p35S-CrDES5 containing the CrDES5 polynucleotide and blunt-ended to give the CrDES5ORF fragment.

Also, a part of pSPB176 was modified and used as a binary vector for constitutive expression. pSPB176 is a vector in which, based on pBINPLUS, the cauliflower mosaic virus 35S (E1235S) promoter (Mitsuhara et al. 1996, Plant Cell Physiol. 37, 49) with repeated enhancer sequence was inserted using HindIII and BamHI and nopaline synthase (nos) terminator was inserted using SalI and EcoRI, and has the ORF of ΔGUS sandwiched between the BamHII and SalI sites.

Next, pSPB176 was digested with BamHI and SalI, and the linear DNA on the vector side was recovered to remove the ORF of ΔGUS. In addition, the blunted CrDES5ORF fragment was inserted into the blunting site of the linear vector to construct pSPB2398, and the construct was provided as a binary vector for constitutive expression of CrDES5. On this plasmid, the CrDES5 polynucleotide is under control of the constitutive promoter.

Throughout the specification, the present invention is explained with reference to the formation of pinolenic acid as an example. However, the polypeptide in accordance with the present invention has, in addition to the activity of Δ5 desaturating linoleic acid to produce pinolenic acid, the activity of Δ5 desaturating α-linolenic acid and the activity of Δ7 desaturating a dienoic or trienoic acid. One skilled in the art will thus readily understand that the present invention is not limited only to the polypeptide and/or polynucleotide in accordance with the present invention as well as the Δ5 desaturation of linoleic acid to produce pinolenic acid, as use thereof.

Example 6

Expression of CrDES5 Polynucleotide in Tobacco and Production of Pinolenic Acid and Coniferonic Acid Subsequently, Agrobacterium tumefaciens (Strain: Agl0, Lazo et al. 1991, BioTechnology, 9, 963) was transformed using pSPB2398, based on the publicly known method (Plant J., 5, 81, 1994). Next, tobacco was transformed by the tobacco leaf disc method (Shimonishi, et al., Shin-Seibutsu Kagaku Jikken-no-Tebiki ((New Guidance of Biochemical Experiment) 3, published by Kagaku Dojin, pp 122-124), using the transformant Agrobacterium bearing this pSPB2398.

RNA was extracted from the obtained transgenic tobacco leaves using RNeasy Plant Minikit (Qiagen). Using the cDNA synthesized from this RNA as template, RT-PCR was performed on Superscript First Strand System (Invitrogen), using as primers the synthetic oligonucleotides CrDES5F 5'-TGTCCCACATTCAGATGGAC-3' (SEQ ID NO: 7) and NosR 5'-ACCGGCAACAGGATTCAATC-3' (SEQ ID NO: 8). The strain in which the CrDES5 polynucleotide was expressed was selected.

Analysis of the fatty acid composition of the transgenic tobacco leaves was conducted by the method described in EXAMPLE 1. In the numerical values, the fatty acid composition is expressed by percentage, along with the total percentage of pinolenic acid and coniferonic acid. For example, in the transgenic tobacco strain N2398-1, pinolenic acid and coniferonic acid that were not detected at all in host (control) reached 19.52% and 21.4% in the total fatty acids. The foregoing results indicate that the gene for Chlamydomonas functions well also in higher plant and the plant which normally does not produce either pinolenic acid or coniferonic acid can be imparted the ability to produce these acids.

TABLE 4

| Strain | Fatty Acid | | | | | | | | | |
| --- | --- | --- | --- | --- | --- | --- | --- | --- | --- | --- |
| | Palitic Acid | 16:1 | 16:3 | Stearic Acid | Oliec Acid | Linoleic Acid | Pinolenic Acid | α-Linoenic Acid | Coniferonic Acid | Pinolenic Acid + Coniferonic Acid |
| Control | 20.12 | 2.34 | 3.57 | 3.29 | 1.20 | 16.95 | 0.00 | 52.54 | 0.00 | 0.00 |
| N2398-1 | 28.49 | 2.50 | 2.74 | 6.21 | 1.34 | 5.47 | 19.52 | 12.34 | 21.40 | 40.92 |
| N2398-2 | 19.62 | 2.17 | 4.09 | 4.79 | 0.00 | 8.04 | 2.36 | 53.70 | 5.23 | 7.59 |
| N2398-3 | 19.80 | 1.93 | 4.36 | 4.11 | 0.00 | 12.43 | 0.00 | 57.37 | 0.00 | 0.00 |
| N2398-4 | 15.92 | 1.63 | 7.42 | 7.28 | 0.00 | 7.81 | 0.00 | 59.93 | 0.00 | 0.00 |
| N2398-5 | 17.42 | 2.04 | 4.21 | 5.54 | 0.00 | 9.48 | 0.00 | 59.04 | 2.29 | 2.29 |
| N2398-6 | 25.19 | 1.01 | 5.79 | 2.61 | 0.00 | 4.86 | 6.32 | 41.32 | 12.88 | 19.20 |
| N2398-7 | 19.30 | 3.50 | 4.34 | 4.60 | 0.00 | 7.41 | 2.11 | 54.04 | 4.71 | 6.82 |
| N2398-8 | 25.88 | 1.44 | 3.59 | 6.65 | 1.11 | 6.54 | 13.14 | 21.01 | 20.63 | 33.78 |
| N2398-9 | 21.33 | 1.46 | 5.73 | 3.01 | 0.00 | 7.82 | 3.09 | 53.56 | 4.00 | 7.09 |
| N2398-10 | 20.13 | 1.96 | 5.68 | 3.54 | 0.00 | 5.79 | 2.56 | 56.49 | 3.85 | 6.41 |
| N2398-11 | 20.89 | 1.31 | 4.41 | 2.84 | 0.00 | 8.97 | 0.00 | 61.59 | 0.00 | 0.00 |
| 2398-1 | 13.60 | 8.49 | 8.97 | 6.83 | 2.19 | 3.24 | 0.00 | 56.68 | 0.00 | 0.00 |
| 2398-2 | 18.67 | 2.02 | 3.47 | 4.32 | 0.00 | 6.76 | 0.00 | 64.76 | 0.00 | 0.00 |
| 2398-3 | 20.66 | 5.27 | 5.54 | 3.30 | 0.00 | 7.19 | 2.12 | 50.86 | 5.07 | 7.18 |
| 2398-4 | 31.46 | 1.30 | 3.58 | 5.71 | 1.44 | 2.84 | 21.26 | 9.07 | 23.34 | 44.60 |
| 2398-5 | 26.70 | 1.76 | 5.03 | 4.75 | 0.66 | 3.82 | 13.71 | 22.21 | 21.35 | 35.07 |

The present invention is not limited to the embodiments described above but may be subject to various modifications within the scope of the claims. In other words, the embodiments which are provided in combination of technical means appropriately modified within the scope of the claims are also deemed to fall within the technical scope of the present invention.

INDUSTRIAL APPLICABILITY

As described above, the polypeptide and polynucleotide in accordance with the present invention are useful for producing pinolenic acid and/or coniferonic acid. Also, the transformant or cell in which the polynucleotide in accordance with the present invention is expressibly introduced is extremely useful in the food sector and various other industries for producing pinolenic acid and/or coniferonic acid or products using them. Furthermore, when the transformant described above is a plant, the plant itself can be used as foodstuff and is thus extremely useful in agricultural sector, and so on.

The invention claimed is:

1. An isolated polynucleotide encoding a polypeptide having a Δ5 fatty acid desaturation activity, wherein the polypeptide comprises:
    (a) the amino acid sequence of SEQ ID NO: 2; or
    (b) the amino acid sequence that has been modified by substitution, deletion, insertion, and/or addition of one to ten amino acids of SEQ ID NO: 2.

2. An isolated polynucleotide, which is either (a) or (b) defined below:
    (a) an isolated polynucleotide consisting of the nucleotide sequence of SEQ ID NO: 1; or,
    (b) an isolated polynucleotide hybridizable to (i) or (ii) below under stringent conditions:
        (i) an isolated polynucleotide consisting of the nucleotide sequence of SEQ ID NO: 1; or,
        (ii) an isolated polynucleotide consisting of the nucleotide sequence complementary to the nucleotide sequence of SEQ ID NO: 1.

3. The polynucleotide of claim 1, which is either (a) or (b) defined below:
    (a) an isolated polynucleotide consisting of the 68th-1498th nucleotide sequence of SEQ ID NO: 1; or,
    (b) an isolated polynucleotide hybridizable to either (i) or (ii) below under stringent conditions:
        (i) an isolated polynucleotide consisting of the 68th-1498th nucleotide sequence of SEQ ID NO: 1; or,
        (ii) an isolated polynucleotide consisting of the nucleotide sequence complementary to the 68th-1498th nucleotide sequence of SEQ ID NO: 1.

4. A vector comprising the polynucleotide of claim 1.

5. A method of producing a polypeptide comprising administering to a cell the vector of claim 4.

6. A non-human transformant transformed with the polynucleotide of claim 1.

7. The transformant of 6, in which the fatty acid composition is modified.

8. The transformant according to claim 6, which is a plant or a progeny of a plant wherein the plant or the progeny is transformed with the polynucleotide of claim 3, or a tissue derived therefrom.

9. The transformant of claim 8, wherein the plant is tobacco or rice.

10. A method of producing a polypeptide comprising culturing the transformant of claim 6.

11. A method of producing a fatty acid comprising extracting a fatty acid from the transformant of claim 6.

12. A cell comprising the vector of claim 4.

13. The cell of 12, which is a cell of rice, tobacco or yeast.

14. A method of producing a polypeptide comprising culturing the cell of claim 12.

15. A method of producing a fatty acid comprising introducing the polynucleotide of claim 1 into a yeast or a plant, and extracting a fatty acid from the yeast or the plant.

16. The method of producing a fatty acid of claim 11, wherein the fatty acid is pinolenic acid or coniferonic acid.

17. A detector comprising the polynucleotide of claim 1 immobilized on a substrate.

* * * * *

SEQUENCE LISTING

<160> NUMBER OF SEQ ID NOS: 8

<210> SEQ ID NO 1
<211> LENGTH: 3154
<212> TYPE: DNA
<213> ORGANISM: Chlamydomonas reinhardtii

<400> SEQUENCE: 1

```
caccgctgaa cgctcgcctt ggtgcttgct ccgtagcaag ctcgggcttc aaacagcgcg      60
aagcaatatg tgcaggccta ccgattccga ctcggggcca gccctgccca gtatcccgca     120
ccagtattgg atcatccatg gtgcaactta cgacctggcc agctatatca agtcgcaccc     180
aggcggcgac gaggccatcc tgctaggacg gggccgcgac tgcactgagc tcttcgagca     240
gtaccatgtg cttaacaaca agcacttgcg tgtgctggag cggttccgcg tcactctgcc     300
ggcggctaag gtggcgacca caacctgaa ggaggacatg gtgtcgacca tcagcgcgtt     360
cgagggcgag gaggcggacg cagcggccgt ggtgggcatc cagcagcctg ctgcacccgc     420
ccgcgttgcg caccagtcgg atccctttta cgaggacatc aaggcaatgg ttcgcgctca     480
cggcaacacc aaaatgtccg ctccgtttgt gatcctccac tgcctgcacg tgtcggcct     540 catctggtct atgaagctgt ggtggcaggg tgccttcatc tcggcattca tcctgcccta     600
tttcctctgg gtgctttgtg cggccatggt gcatgatggc gggcacttcg cacacagcaa     660
gcggccactc gtcaacaagc tgctgacgca cacggtgcc ctcttcacca acagcgtggg     720
ctgctggtac ctgcagcaca acatcctgca ccactcctac accaacctgg tcggcaagga     780
```

```
cggcgacctg gactcgcacc acccctacat gcgcatccac ccggagcagt ccatgctccc    840
cgccaacatc caccacgccg tccgcttctt cagccacctc atcatgtaca acttcgcgca    900
catcggcctg accatgatct cgccccttag ctacttccgc ggcgtggccg cgcagaagaa    960
gggcaccgcc gacgccaagc aggcgcagga cgcgcagacg gtggcgcagt accacagcac   1020
cgtgatgctg cagttggtga cggtgggggc gttctacatc acgcccttcc tgcgcttcga   1080
cttcagccgc gcgctgctgc tgacgctgct gcccaccttc atgatgagcg tggccttcat   1140
ggtgattgcc caggtgtccc acattcagat ggacgcggag gcgccctccg ccgacctgga   1200
gaagctgcac tgggcccgcc gcatggcgct cacgtccgtg gactactcgc aggagtcgac   1260
gctgtgggcc tacctgacca tcgggctcaa catgcagtcg ctgcaccaca tcgtgccggg   1320
cgtgtcgtac agccaacttc cgcgcctgta ccctgcctac cgcgccatct gcgagaagca   1380
cggcatcaag ctgctggagc gccgcaacct ggcgcacgcc ttctggacgc acctgcagac   1440
gctgtgggtg ctgtccaaga cgcacagctt tgtgagggtg gcgcgcaagc tggcgtaaag   1500
gaggagaggt gcaggcgcgg cggctggggc gcaagcgctg gcgtgcggag gagcgtgcaa   1560
actgcaaagc agcgcttctt ctcgcggccg ttgcacttgt gtagatgccc tggcgagagc   1620
ggtggctgat ttgattgcat ctggcgcaag cagcttggtc acggcgacgg ccttggggtg   1680
tgaagtatgg ggcgtcagtc agtgggccgc gggtgtggca cctgctcgca gcagtaatat   1740
cttggatttg tggccttgtg gccatgcact ccatacaacg gtgatacggt agcggcggct   1800
ccgggcttgc gaaaagacat catctcgagc gcggtcccga gggagcaccg cgtctcctgc   1860
acggcacctc ctgccgtgcg agggagcgag tatctgtaaa tgcaagctgg tgcgtttacg   1920
tgcgtgtggt gtgtggttgg ttatgggcgt tgagctggac cggaccccg gcgcagtgcg    1980
cgacgggtgg gcacgggtgt ggcgcatccg tggctgtgtg cgttgctgcg tttacatctc   2040
tgcgtgcgtg cacagaggtg agttcaatga tttgtgccag tcttgatgtc ggtggcggta   2100
acaacaacaa taagtttgca tggtgttgt ggaagtctac gtggctggtc gagtgggcgg    2160
cctgcgagtc cgaacggagg cccccgcatt acaaagaaga agaatcacgc aatgcacaga   2220
gtcttgagct gaggatgtgc tgtacacggg tgtttagttt gggtgtagtt ctctctcgtt   2280
gttgtggtag tgtgtggtgc gaaggtgtgt gtctgtgctg agtaagccgc ccctcgacg    2340
cagtgtgtgg agatcgtggt ttggtgttgt acccgagcgg gaggcaggcc cgggcctggc   2400
ctgctgagcg tggccggctg tgaggaagcg tgtgtgcccg gccggctttg ttgttgtgac   2460
agcgattggc ggcgaccggg cgtggtcccg ggggaagagg agaggagcag aggcaggagt   2520
agacaagagc ccaaggcgcg aatgggtggg cggcggcaga ggagcgtgac tggtgcacgc   2580
aaacacatag gattcatttg ggtccggggt gcgctgatga gcggaggggg gttgctcggg   2640
gaggccagca gaaggtgcgc cctcggccca gggcgatctg cgtgacactt gaattgcacg   2700
attagggtct tgcattaggc gcatgaatgt acgggctagg atgtatttgt gagtcatgcg   2760
aggcgtagcg agtagcgcgt tgaaggtagg tgatcgcggt gtaggtccat ttcttttacc   2820
acagcgtcga ggttcgggca ccggcagatg ccgtgatgac ggcagatgcc gtgatgatgg   2880
cgcgacggcg aacacaaact caatacccgt gtggaggtgt gggagcggac gcgatggcgc   2940
cgagtgggga gtgcgggcac tggcaggcgg cacacggatg ctgctgcgtg cacgaggcgg   3000
gatggcgcgc agggctggcc gctggccgcc tacggtgtgg taccaacagg tctgccccgg   3060
caggtgctgg gccggctcgg aggagattgc gtttacggta gttatctgga ctgtaaagga   3120
ctgatcgcga aaaaaaaaaa aaaaaaaaaa aaaa                               3154
```

```
<210> SEQ ID NO 2
<211> LENGTH: 476
<212> TYPE: PRT
<213> ORGANISM: Chlamydomonas reinhardtii

<400> SEQUENCE: 2

Met Cys Arg Pro Thr Asp Ser Asp Ser Gly Pro Ala Leu Pro Ser Ile
  1               5                  10                  15

Pro His Gln Tyr Trp Ile Ile His Gly Ala Thr Tyr Asp Leu Ala Ser
                 20                  25                  30

Tyr Ile Lys Ser His Pro Gly Gly Asp Glu Ala Ile Leu Leu Gly Arg
             35                  40                  45

Gly Arg Asp Cys Thr Glu Leu Phe Glu Gln Tyr His Val Leu Asn Asn
         50                  55                  60

Lys His Leu Arg Val Leu Glu Arg Phe Arg Val Thr Leu Pro Ala Ala
 65                  70                  75                  80

Lys Val Ala Thr Asn Asn Leu Lys Glu Asp Met Val Ser Thr Ile Ser
                 85                  90                  95

Ala Phe Glu Gly Glu Glu Ala Asp Ala Ala Val Val Gly Ile Gln
                100                 105                 110

Gln Pro Ala Ala Pro Ala Arg Val Ala His Gln Ser Asp Pro Phe Tyr
            115                 120                 125

Glu Asp Ile Lys Ala Met Val Arg Ala His Gly Asn Thr Lys Met Ser
        130                 135                 140

Ala Pro Phe Val Ile Leu His Cys Leu His Val Val Gly Leu Ile Trp
145                 150                 155                 160

Ser Met Lys Leu Trp Trp Gln Gly Ala Phe Ile Ser Ala Phe Ile Leu
                165                 170                 175

Pro Tyr Phe Leu Trp Val Leu Cys Ala Ala Met Val His Asp Gly Gly
                180                 185                 190

His Phe Ala His Ser Lys Arg Pro Leu Val Asn Lys Leu Leu Thr His
            195                 200                 205

Thr Gly Ala Leu Phe Thr Asn Ser Val Gly Cys Trp Tyr Leu Gln His
        210                 215                 220

Asn Ile Leu His His Ser Tyr Thr Asn Leu Val Gly Lys Asp Gly Asp
225                 230                 235                 240

Leu Asp Ser His His Pro Tyr Met Arg Ile His Pro Glu Gln Ser Met
                245                 250                 255

Leu Pro Ala Asn Ile His His Ala Val Arg Phe Phe Ser His Leu Ile
                260                 265                 270

Met Tyr Asn Phe Ala His Ile Gly Leu Thr Met Ile Ser Pro Leu Ser
            275                 280                 285

Tyr Phe Arg Gly Val Ala Ala Gln Lys Lys Gly Thr Ala Asp Ala Lys
        290                 295                 300

Gln Ala Gln Asp Ala Gln Thr Val Ala Gln Tyr His Ser Thr Val Met
305                 310                 315                 320

Leu Gln Leu Val Thr Val Gly Ala Phe Tyr Ile Thr Pro Phe Leu Arg
                325                 330                 335

Phe Asp Phe Ser Arg Ala Leu Leu Leu Thr Leu Leu Pro Thr Phe Met
                340                 345                 350

Met Ser Val Ala Phe Met Val Ile Ala Gln Val Ser His Ile Gln Met
            355                 360                 365

Asp Ala Glu Ala Pro Ser Ala Asp Leu Glu Lys Leu His Trp Ala Arg
        370                 375                 380
```

Arg Met Ala Leu Thr Ser Val Asp Tyr Ser Gln Glu Ser Thr Leu Trp
385                 390                 395                 400

Ala Tyr Leu Thr Ile Gly Leu Asn Met Gln Ser Leu His His Ile Val
            405                 410                 415

Pro Gly Val Ser Tyr Ser Gln Leu Pro Arg Leu Tyr Pro Ala Tyr Arg
        420                 425                 430

Ala Ile Cys Glu Lys His Gly Ile Lys Leu Leu Glu Arg Arg Asn Leu
    435                 440                 445

Ala His Ala Phe Trp Thr His Leu Gln Thr Leu Trp Val Leu Ser Lys
450                 455                 460

Thr His Ser Phe Val Glu Val Ala Arg Lys Leu Ala
465                 470                 475

```
<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 3
gccgaattca atatgtgcag gcctaccg                                      28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 4
gccgaattct tacgccagct tgcgcgcc                                      28

<210> SEQ ID NO 5
<211> LENGTH: 19
<212> TYPE: DNA
<213> ORGANISM: Chlamydomonas reinhardtii

<400> SEQUENCE: 5
aatatgtgca ggcctaccg                                                19

<210> SEQ ID NO 6
<211> LENGTH: 19
<212> TYPE: DNA
<213> ORGANISM: Chlamydomonas reinhardtii

<400> SEQUENCE: 6
ttacgccagc ttgcgcgcc                                                19

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 7
tgtcccacat tcagatggac                                               20

<210> SEQ ID NO 8
```

```
<211> LENGTH: 20
<212> TYPE: DNA
<213> ORGANISM: Artificial Sequence
<220> FEATURE:
<223> OTHER INFORMATION: Description of Artificial Sequence:Artificially
      Synthesized Primer Sequence

<400> SEQUENCE: 8
accggcaaca ggattcaatc                                                    20
```